United States Patent
Kim et al.

(10) Patent No.: US 12,344,636 B2
(45) Date of Patent: Jul. 1, 2025

(54) RESPIRATORY SYNCYTIAL VIRUS RECOMBINANT F PROTEIN AND VACCINE COMPOSITION CONTAINING SAME

(71) Applicant: SK BIOSCIENCE CO., LTD., Seongnam-si (KR)

(72) Inventors: Eun-som Kim, Seongnam-si (KR); Teawoo Kwon, Seongnam-si (KR); Ki-weon Seo, Seongnam-si (KR); Seung-hye Hong, Seongnam-si (KR); Su Jeen Lee, Seongnam-si (KR); Dong Soo Ham, Seongnam-si (KR); Hun Kim, Seongnam-si (KR)

(73) Assignee: SK BIOSCIENCE CO., LTD., Seongnam-si (KR)

( * ) Notice: Subject to any disclaimer, the term of this patent is extended or adjusted under 35 U.S.C. 154(b) by 107 days.

(21) Appl. No.: 17/290,384

(22) PCT Filed: Nov. 1, 2019

(86) PCT No.: PCT/KR2019/014755
§ 371 (c)(1),
(2) Date: Apr. 30, 2021

(87) PCT Pub. No.: WO2020/091529
PCT Pub. Date: May 7, 2020

(65) Prior Publication Data
US 2022/0073566 A1 Mar. 10, 2022

(30) Foreign Application Priority Data
Nov. 1, 2018 (KR) .................. 10-2018-0133084

(51) Int. Cl.
C07K 14/005 (2006.01)
A61K 39/00 (2006.01)
A61K 39/155 (2006.01)
A61P 31/14 (2006.01)

(52) U.S. Cl.
CPC .......... *C07K 14/005* (2013.01); *A61K 39/155* (2013.01); *A61P 31/14* (2018.01); *A61K 39/00* (2013.01); *C07K 2319/735* (2013.01); *C12N 2760/18522* (2013.01); *C12N 2760/18534* (2013.01); *C12N 2760/18571* (2013.01)

(58) Field of Classification Search
CPC ............ C07K 14/005; C07K 2319/735; C07K 14/255; C07K 2319/00; C07K 2319/70; A61K 39/155; A61K 39/00; A61K 2039/55505; A61K 2039/6075; A61K 2039/70; A61K 39/0275; A61K 39/12; A61K 2039/5256; A61P 31/14; C12N 2760/18522; C12N 2760/18534; C12N 2760/18571; C12N 2710/14143; C12N 2795/10122; C12N 2795/10111; Y02A 50/30
See application file for complete search history.

(56) References Cited

U.S. PATENT DOCUMENTS

| | | | |
|---|---|---|---|
| 2011/0305727 A1 | 12/2011 | Swanson et al. | |
| 2014/0248313 A1 | 9/2014 | van den Hurk et al. | |
| 2014/0271699 A1* | 9/2014 | Kwong | C07K 14/005 435/254.11 |
| 2016/0176932 A1* | 6/2016 | Langedijk | A61P 31/12 435/254.2 |
| 2016/0324958 A1 | 11/2016 | Burkhard et al. | |
| 2018/0271970 A1* | 9/2018 | Ciaramella | A61K 31/7115 |

FOREIGN PATENT DOCUMENTS

| | | |
|---|---|---|
| WO | 2005042564 A1 | 5/2005 |
| WO | 2008/114149 A2 | 9/2008 |
| WO | 2009128951 A1 | 10/2009 |
| WO | 2010/077717 A1 | 7/2010 |
| WO | 2019066437 A1 | 4/2019 |

OTHER PUBLICATIONS

Chen X, Zaro JL, Shen WC. Fusion protein linkers: property, design and functionality. Adv Drug Deliv Rev. Oct. 2013;65(10):1357-69. Epub Sep. 29, 2012. (Year: 2013).*
Taleb SA, Al Thani AA, Al Ansari K, Yassine HM. Human respiratory syncytial virus: pathogenesis, immune responses, and current vaccine approaches. Eur J Clin Microbiol Infect Dis. Oct. 2018;37(10):1817-1827. Epub Jun. 6, 2018. (Year: 2018).*
Falloon J, Yu J, Esser MT, Villafana T, Yu L, Dubovsky F, Takas T, Levin MJ, Falsey AR. An Adjuvanted, Postfusion F Protein-Based Vaccine Did Not Prevent Respiratory Syncytial Virus Illness in Older Adults. J Infect Dis. Dec. 12, 2017;216(11):1362-1370. (Year: 2017).*
NIAID. NIAID Research Journeys: safe and effective RSV protein vaccines. May 1, 2023. (Year: 2023).*
McLellan JS, Chen M, Joyce MG, Sastry M, Stewart-Jones GB, Yang Y, Zhang B, Chen L, Srivatsan S, Zheng A, Zhou T, et. al. Structure-based design of a fusion glycoprotein vaccine for respiratory syncytial virus. Science. Nov. 1, 2013;342(6158):592-8. Erratum in: Science. Nov. 22, 2013;342(6161):931. (Year: 2013).*

(Continued)

*Primary Examiner* — Rachel B Gill
(74) *Attorney, Agent, or Firm* — MH2 Technology Law Group, LLP

(57) ABSTRACT

The present invention provides a respiratory syncytial virus (RSV) recombinant fusion protein (F protein) in which a polymerization domain derived from a foreign protein is bound to the C terminal of a fusion protein (F protein) lacking a transmembrane domain of a wild-type respiratory syncytial virus (RSV) fusion protein (F protein). The recombinant fusion protein of the present invention is soluble and can retain an F protein trimer. Excellent immune-inducing effects can be expected from the recombinant fusion protein of the present invention, and vaccine composition containing same.

16 Claims, 7 Drawing Sheets
Specification includes a Sequence Listing.

(56) References Cited

OTHER PUBLICATIONS

Swanson et al., "Structural basis for immunization with postfusion respiratory syncytial virus fusion F glycoprotein (RSV F) to elicit high neutralizing antibody titers", Proceedings of the National Academy of Sciences, vol. 108, No. 23, 2011, pp. 9619-9624.
International Search Report dated Feb. 25, 2020 for International Patent Application No. PCT/KR2019/014755 (Examiner, Unknown), 12 pages with English translation.
Martin et al., "Sequence elements of the fusion peptide of human respiratory syncytial virus fusion protein required for activity", Journal of General Virology, 2006, vol. 87, pp. 1649-1658.

* cited by examiner

FIG. 9

Induction immune responses of RSV post tagging antigen (neutralizing antibody titer)

RESPIRATORY SYNCYTIAL VIRUS RECOMBINANT F PROTEIN AND VACCINE COMPOSITION CONTAINING SAME

CROSS-REFERENCE TO RELATED APPLICATIONS

The present application is a U.S. National Stage application of PCT/KR2019/014755 filed on Nov. 1, 2019, which claims priority to Korean Patent Application No. 10-2018-0133084 filed on Nov. 1, 2018 in the Republic of Korea, the disclosures of which are incorporated herein by reference.

TECHNICAL FIELD

The present disclosure relates to a fusion protein (F protein) of recombinant respiratory syncytial virus (RSV) and an immunogenic composition containing the same, particularly to a fusion protein (F protein) of recombinant respiratory syncytial virus (RSV), capable of expressing the RSV fusion protein in large quantities and inducing specific neutralizing antibodies, and an immunogenic composition containing the same.

SEQUENCE LISTING

The instant application contains a Sequence Listing which has been submitted electronically in ASCII format and is hereby incorporated by reference in its entirety. Said ASCII copy, created on Dec. 31, 2024, is named 0393.0009-US Sequence Listing_ST.25.txt and is 477,316 bytes in size.

BACKGROUND ART

Respiratory syncytial virus (RSV) is a globally prevalent virus, which causes respiratory diseases and is the major cause of death of children due to severe respiratory infection. Although children are the main target of infection, it is known that it can cause fatal respiratory diseases in patients and the elderly with weak immune functions. Although it is the second cause of respiratory diseases next to influenza, it is known that the annual mortality rate of RSV per 100,000 children below 1 year of age is about 1.3-2.5 times higher than influenza. According to the WHO's report in 2002, 64 million people are infected with RSV each year, and 169,000 out of them die.

For defense against the RSV disease, an inactivated vaccine using inactivated virus was developed at first. However, the use of the inactivated vaccine became impossible due to severe side effects such as aggravation of the symptoms of the disease. There have been efforts to develop a live vaccine, but there are many difficulties in the development because of the metastability and safety problems of the virus. The major antigens of RSV infection are glycoprotein (G protein) and fusion protein (F protein), which are surface proteins. These two proteins are known to play important roles in defense and prevention of viral infection. As the F protein is reported to be more effective in defense against virus, the development of a vaccine using the F protein is being attempted actively. The RSV F protein is an important constituent which fuses with the cell membrane during the early stage of virus entry and is known as the main target of vaccines and antiviral drugs due to high antigenicity. The F protein of RSV is refolded from a "pre-fusion" conformation to a "post-fusion" conformation during entry into a cell.

The F protein consists of about 574 amino acids. The full-length F protein F0 can be divided into F2 (~20 kDa) and F1 (~50 kDa) subunits. Three is a furin cleavage site between the subunits F2 and F1, where the protein is cleaved into F2 and F1 by a furin-based protease. In furin cleavage, the amino acid sequences of two sites "RARR" (SEQ ID NO: 102) and "KKRKRR" (SEQ ID NO: 103) are recognized, where arginine (R) functions as a core amino acid. Heptad repeat regions exist at the N-terminal and C-terminal of the F1 subunit. The heptad repeat region existing at the N-terminal is called HRA, and the heptad repeat region existing at the C-terminal is called HRB. The transformation and cell-virus fusion of the F protein occur as the bent hinge of HRA is spread. In addition, it was found out that trimer formation is induced as the p27 domain is removed by furin cleavage. When the virus comes in contact with a host cell, a harpoon-like structure is put into the cell membrane as the structure of the F protein on the virus surface is changed. Then, the virus is pulled toward the virus, causing the cell membranes to merge. As a result of the fusion, the RNA genome of the virus enters the cell and begins replication. Accordingly, the structural change of the F protein during the fusion process is the key to the understanding of the virus's invasion mechanism. Upon infection by RSV, the F protein is transformed from the pre-fusion conformation to the post-fusion conformation during the process of cell membrane fusion. If the F protein of the virus is transformed to the post-fusion conformation prior to infection (cell fusion), the infectivity is lost.

Due to this characteristic, many researches on stabilizing the F protein in the pre-fusion conformation and increasing the immunogenicity of the F protein are ongoing. When the wild-type F protein is produced as a recombinant protein, it is mostly produced an insoluble form. The insoluble F protein has the problems that purification is difficult, mass expression is impossible because the proper protein structure cannot be formed, and the protein cannot serve as an antigen for inducing immune responses effective for protection against viruses.

Therefore, the inventors of the present disclosure have studied on a novel RSV fusion protein for inducing RSV immune responses, which serves as an antigen capable of inducing RSV immune responses, is easy to purify, and can be easily expressed in large quantities.

DISCLOSURE

Technical Problem

The present disclosure is directed to providing a recombinant RSV F protein.

The present disclosure is also directed to providing a soluble recombinant respiratory syncytial virus (RSV) fusion (F) protein having superior immunogenicity-inducing ability.

The present disclosure is also directed to providing a novel method capable of increasing immunogenicity while increasing protein expression level by providing a soluble RSV F protein.

The present disclosure is also directed to providing an RSV immunogen and a method for preparing the same.

The present disclosure is also directed to providing a novel method capable of increasing the antigenicity of an RSV vaccine.

The present disclosure is also directed to providing a soluble RSV F protein, a nucleic acid molecule encoding the same, a composition for inducing immunogenicity, and a use of a soluble RSV F protein for inducing immune responses in animals and human, particularly a use thereof as a vaccine.

Technical Solution

Definition of General Terms

Unless defined otherwise in the present disclosure, all the technical terms used to describe the present disclosure have the same meanings as those generally understood by those of ordinary skill in the art to which the present disclosure belongs.

The term "F protein" or "fusion protein" used in the present disclosure refers to a polypeptide or a protein having all or part of the amino acid sequence of the RSV fusion protein. The term "G protein" used in the present disclosure refers to a polypeptide or a protein having all or part of the amino acid sequence of the RSV attachment protein polypeptide. Numerous RSV fusion and attachment proteins are known to those skilled in the art. WO2008/114149 describes exemplary F and G protein variants (e.g., naturally occurring variants) that are publicly available.

The term "protein" or "polypeptide" used in the present disclosure refers to an aggregate of amino acids produced by encoding of specific nucleic acids. Here, the aggregate refers to a unit consisting of two, three, four or more amino acids. The "protein" or "polypeptide" includes not only naturally occurring proteins but also those produced through recombination or synthesis. The term "fragment" refers to a part of a polypeptide (i.e., a subsequence). In general, the arrangement of a polypeptide is represented in a direction of N-terminal→C-terminal defined by the arrangement of the amino and carboxy residues of individual amino acids. The polypeptide is translated from the N (amino)-terminal toward the C (carboxy)-terminal.

The term "recombinant" protein used in the present disclosure refers to a protein encoded by a heterologous (e.g., recombinant) nucleic acid introduced into a host cell, e.g., a bacterial or eukaryotic cell. That is to say, it refers to a protein which has been genetically modified to be produced in large quantities.

The term "domain" of a polypeptide or a protein used in the present disclosure refers to a structurally or functionally defined element in a polypeptide or a protein. For example, a "polymerization domain" is an amino acid sequence in a polypeptide which enhances assembling of monomers into a polymer. For example, the polymerization domain may enhance the assembling to a polymer through association with another polymerization domain (the polymerization domain of an additional polypeptide having the same or different amino acid sequence). The term is also used to refer to a polynucleotide encoding such a peptide or polypeptide. In addition, the polymerization domain may refer to a trimerization domain, which helps the RSV F protein of the present disclosure to be assembled into a trimer.

The term polymerization domain "derived from a heterologous protein" used in the present disclosure is understood to mean a domain derived from species other than RSV virus (e.g., viruses other than the RSV virus, bacteria, bacteriophages, etc.), which helps the RSV F protein in soluble state to be assembled into a trimer.

The term "immunogen" or "antigen" used in the present disclosure is understood to mean any substance having the immunogenicity of inducing or causing immune response in a host cell. For example, it includes such substances as a protein, a peptide or a nucleic acid. Here, the immunogenicity of inducing or causing immune response includes both cellular immunity and humoral immunity. The term "antigen" includes, for example, all or part of a foreign substance that has infiltrated into the body and may be understood to mean all or part of a recombinant RSV F protein. The term induction of immunity by an "antigen" may be understood to mean the formation of an antigen-specific antibody.

The antigen-specific antibody includes a neutralizing antibody which defends a cell from a substance that has infiltrated from outside through neutralization.

The term "vaccine" used in the present disclosure refers to a preparation of an induced antigenic determinant, which is used to induce antibody production or immunity against a pathogen. The vaccine provides immunity against diseases caused by various types of viruses (e.g., influenza, etc.). The term "vaccine" also refers to a suspension or a solution of an immunogen (e.g., modified or mutated RSV F protein) that is administered to a vertebrate to produce protective immunity, i.e., immunity that prevents or reduces the severity of a disease associated with infection. The present disclosure provides a vaccine composition which is immunogenic and can provide protection against a disease associated with infection.

The term "immune response" used in the present disclosure refers to a response of a cell of the immune system, e.g., a B cell, a T cell or a monocyte, in response to stimulus. The immune response may be a B cell response which causes the production of a specific antibody, e.g., an antigen-specific neutralizing antibody. In addition, the immune response may be a T cell response, e.g., a CD4+ response or a CD8+ response. In some cases, the response is specific for a particular antigen (i.e., "antigen-specific response"). When the antigen is derived from a pathogen, the antigen-specific response is a "pathogen-specific response". A "protective immune response" is an immune response that inhibits the detrimental function or activity of a pathogen, reduces infection by a pathogen, or decreases symptoms (including death) resulting from infection by a pathogen.

Polymerization Domain Derived from Heterologous Protein

As stated above in the definition of general terms, a polymerization domain derived from a heterologous protein is derived from a heterologous species (e.g., virus, bacteria, bacteriophage, etc.) other than the RSV virus, and may refer to a polypeptide domain. In the present disclosure, the polymerization domain is understood to mean a peptide domain which helps the RSV F protein in soluble state to be assembled into a trimer.

The polymerization domain may exist as various forms which can stabilize the protein structure. In a specific exemplary embodiment of the present disclosure, it may be a foldon polymerization domain derived from the bacteriophage T4 fibritin.

The inventors of the present disclosure have identified that binding with the foldon domain may lead to improved trimerization yield. In addition, they have found out that the binding with the foldon domain leads to easier protein purification and increased total antibody titer and neutralizing antibody titer. The inventors of the present disclosure have aimed at remarkably improving trimerization yield by binding the heterologous trimerization domain to the postfusion F protein.

The foldon domain may be a foldon domain of the fibritin protein of bacteriophage T4. It adopts a β-propeller conformation, and can fold and trimerize in an autonomous way. Although the soluble fusion protein (F protein) with a transmembrane domain removed exists predominantly as monomers, the soluble fusion protein (F protein) with the transmembrane domain removed may be stabilized as trimers by fusing foldon at the C-terminal. The foldon-bound recombinant fusion protein of the present disclosure may exist as a trimeric recombinant fusion protein. As a specific example, the soluble post-fusion F protein with the foldon domain bound may be used as an antigen. The recombinant fusion protein of the present disclosure which exists as a trimer may provide superior neutralizing antibody titer.

In addition, it is expected that the recombinant fusion protein with foldon bound can induce an antibody for a specific major neutralizing epitope as compared to the monomer fusion protein without foldon.

In another exemplary embodiment of the present disclosure, the foldon domain may be linked to the flagellin protein. More specifically, the foldon domain may be linked to the D1 domain of the flagellin protein.

In another exemplary embodiment, the flagellin protein (particularly, the D1 domain of the flagellin protein) may be linked instead of the foldon domain. The D1 domain of the flagellin protein may be a recombinant D1 domain.

The linkage between the foldon domain and the flagellin protein may be achieved, for example, by i) linking the foldon domain first at the C-terminal of the fusion protein (F protein) with the transmembrane domain at amino acids 525-574 of the wild-type respiratory syncytial virus (RSV) fusion protein (F protein) of SEQ ID NO: 1 deleted and then linking the D1 domain of the flagellin protein, or ii) linking the foldon domain and the D1 domain of the flagellin protein first and then binding at the C-terminal of the fusion protein (F protein) with the transmembrane domain at amino acids 525-574 of the wild-type respiratory syncytial virus (RSV) fusion protein (F protein) of SEQ ID NO: 1 deleted.

Specifically, since flagellin is a protein with very low similarity between bacterial species, its effect may be different depending on which domain of which species is used. For fusion with the recombinant RSV F protein of the present disclosure, it is preferred use the D1 domain of the flagellin protein only. Since the D1 domain includes a TLR5-binding site, it is expected that antigen-specific CD4+ T cell response and strong humoral response will be induced by such mechanisms as NF-kB activation, TLR5-expressing CD11c+ cell stimulation, etc. The flagellin protein is the flagellin protein of *Salmonella enterica*. *Salmonella enterica* often exhibits various characteristics such as host specificity, antibiotic resistance, etc. depending on serotype. For example, the flagellin protein encoded by the FliC gene possessed by the serotype group D (Dublin) of *Salmonella enterica* ssp. *enterica* may be included in the scope of the present disclosure. In addition, the flagellin protein encoded by the FliC gene possessed by the serotype group D (Dublin) of *Salmonella enterica* ssp. *enterica* may be designed newly for use as a recombinant fusion protein. The flagellin D1 domain was designed by linking amino acids 54-176 at the N-terminal of the D1 domain and amino acids 413-454 at the C-terminal with a linker G, and was named as the recombinant D1 domain polypeptide of the flagellin protein (see SEQ ID NO: 24). The recombinant D1 domain polypeptide was codon-optimized for easier expression in insect cells (SEQ ID NO: 94).

When only the recombinant D1 domain polypeptide is linked, it may be more advantageous in terms of protein expression, trimer structure formation, etc. as compared to when the full flagellin protein is linked because the protein size is decreased and a more compact structure can be formed while maintaining the effect of flagellin.

Preparation of Recombinant Fusion Protein of Respiratory Syncytial Virus

In an exemplary embodiment, the present disclosure provides a new type of recombinant fusion protein with the transmembrane domain of the wild-type respiratory syncytial virus (RSV) fusion protein (F protein) deleted and the fusion protein modified by linking a new domain. Hereinafter, the new type of recombinant fusion protein with the fusion protein modified means a 'recombinant fusion protein of respiratory syncytial virus' and is referred to as RFP-RSV (recombinant fusion protein of RSV).

In another exemplary embodiment, the present disclosure provides a new type of recombinant fusion protein with the transmembrane domain of the wild-type respiratory syncytial virus (RSV) fusion protein (F protein) deleted and the amino acid sequence of the fusion peptide domain (FP domain) of the fusion protein (F protein) modified.

In the present disclosure, the respiratory syncytial virus fusion protein (F protein) is distinguished from the wild-type respiratory syncytial virus (RSV) fusion protein (F protein).

The recombinant fusion protein (F protein) of the respiratory syncytial virus (RSV) of the present disclosure means a soluble fusion protein with the transmembrane domain of the wild-type RSV F protein deleted and the amino acid sequence of the fusion peptide domain (FP domain) modified. In an exemplary embodiment, the variation of the amino acid sequence of the fusion peptide domain (FP domain) may occur at the FLGFLLGVG (SEQ ID NO: 104) amino acid sequence of the FP domain. Hereinafter, the F protein with the transmembrane domain of the F protein deleted and one or more amino acid substitution induced may be named as sF protein (soluble fusion protein).

The fusion protein of the wild-type respiratory syncytial virus may include SEQ ID NO: 1 or an amino acid sequence which is 80%, specifically 85%, more specifically 90%, further more specifically 95%, identical to the sequence of SEQ ID NO: 1. In an exemplary embodiment of the present disclosure, the fusion protein with a 'polymerization domain derived from a heterologous protein' linked may have the transmembrane domain of the wild-type RSV F protein deleted, and is specifically represented by SEQ ID NO: 2. The transmembrane domain may be located at amino acid sequences 525-574.

In an exemplary embodiment of the present disclosure, the fusion protein with a 'polymerization domain derived from a heterologous protein' linked may have the transmembrane domain of the wild-type RSV F protein deleted, and may further have the FLGFLLGVG (SEQ ID NO: 104) sequence at positions 137-145 of SEQ ID NO: 2 modified. The amino acid sequences 137-145 of SEQ ID NO: 2 may be included in the fusion peptide domain (FP domain).

In an exemplary embodiment of the present disclosure, the fusion protein with a 'polymerization domain derived from a heterologous protein' linked may have the transmembrane domain at amino acid sequences 525-574 of the wild-type RSV F protein deleted, may further have the FLGFLLGVG (SEQ ID NO: 104) sequence at positions 137-145 of SEQ ID NO: 2 modified, and the FLGFLLGVG (SEQ ID NO: 104) sequence may be substituted with i) AAGAAAGAG (SEQ ID NO: 95), ii) QNGQNNGSG (SEQ ID NO: 96), iii) NSGNSSGGG (SEQ ID NO: 97), or iv) TLSKKKRKRR (SEQ ID NO: 98). Specifically, the fusion protein may be represented by SEQ ID NO: 3, 4, 5 or 6.

In an exemplary embodiment of the present disclosure, the fusion protein with a 'polymerization domain derived from a heterologous protein' linked may have the transmembrane domain of the wild-type RSV F protein deleted, and may have one or more amino acid substitution in the amino acid sequence of SEQ ID NO: 2. Specifically, the amino acid substitution may occur at one location.

The fusion protein may have amino acid substitution at the following positions of the amino acid sequence of SEQ ID NO: 2:
(a) substitution of the amino acid residue F at 140th position with W;
(b) substitution of the amino acid residue E at the 163rd position with Q;
(c) substitution of the amino acid residue V at the 179th position with L;
(d) substitution of the amino acid residue L at the 188th position with Q;
(e) substitution of the amino acid residue T at the 189th position with L;
(f) substitution of the amino acid residue E at the 487th position with L; or
(g) substitution of the amino acid residue F at the 505th position with W.

The above-described substitutions (a)-(g) are preferred because soluble RSV can be obtained through the amino acid substitutions at the specified locations of the amino acid sequence of SEQ ID NO: 2.

For example, the sF protein includes, on the basis of SEQ ID NO: 2, one or more substitution selected from a group consisting of:
(a) substitution of the amino acid residue F at the 140th position with W (SEQ ID NO: 7);
(b) substitution of the amino acid residue E at the 163rd position with Q (SEQ ID NO: 8);
(c) substitution of the amino acid residue V at the 179th position with L (SEQ ID NO: 9);
(d) substitution of the amino acid residue L at the 188th position with Q (SEQ ID NO: 10);
(e) substitution of the amino acid residue T at the 189th position with L (SEQ ID NO: 11);
(f) substitution of the amino acid residue E at the 487th position with L (SEQ ID NO: 12); and
(g) substitution of the amino acid residue Fat the 505th position with W (SEQ ID NO: 13).

In another exemplary embodiment, the sF protein may have, on the basis of SEQ ID NO: 2,
the amino acid corresponding to the 140th position substituted with W, and the amino acid corresponding to the 163th position substituted with Q (SEQ ID NO: 14);
the amino acid corresponding to the 140th position substituted with W, the amino acid corresponding to the 163th position substituted with Q, the amino acid corresponding to the 188th position substituted with Q, and the amino acid corresponding to the 189th position substituted with L (SEQ ID NO: 15);
the amino acid corresponding to the 488th position substituted with W, and the amino acid corresponding to the 163rd position substituted with Q (SEQ ID NO: 16);
the amino acid corresponding to the 488th position substituted with W, and the amino acid corresponding to the 179th position substituted with L (SEQ ID NO: 17);
the amino acid corresponding to the 140th position substituted with W, and the amino acid corresponding to the 505th position substituted with W (SEQ ID NO: 18);
the amino acid corresponding to the 487th position substituted with L, and the amino acid corresponding to the 505th position substituted with W (SEQ ID NO: 19);
the amino acid corresponding to the 163rd position substituted with Q, and the amino acid corresponding to the 505th position substituted with W (SEQ ID NO: 20);
the amino acid corresponding to the 188th position substituted with Q, the amino acid corresponding to the 189th position substituted with L, and the amino acid corresponding to the 505th position substituted with W (SEQ ID NO: 21); or
the amino acid corresponding to the 163rd position substituted with Q, and the amino acid corresponding to the 487th position substituted with L (SEQ ID NO: 22).

In an exemplary embodiment of the present disclosure, an RSV F protein with a part of the fusion peptide (F protein) of the wild-type respiratory syncytial virus (RSV) deleted may be represented by SEQ ID NO: 2, and the RSV F protein of SEQ ID NO: 2 may be provided as an RSV immunogen or an antigen for inducing immunity against RSV.

The inventors of the present disclosure have further found out that excellent neutralizing antibody-inducing ability is achieved when the polypeptide of the foldon domain or the foldon domain-flagellin protein (particularly D1 domain) is further linked.

The RSV F protein of SEQ ID NO: 2 includes one with the amino acid sequences 525-574 of the wild-type RSV F protein of SEQ ID NO: 1 deleted.

The inventors of the present disclosure have developed through researches for a long period of time a recombinant RSV F protein immunogen capable of providing excellent neutralizing antibody titer through one, two or more sequence variation of the fusion peptide of the RSV F protein.

The RFP-RSV of the present disclosure may be used for prevention, treatment, etc. of RSV infection, and specifically may be provided as a vaccine for prevention of RSV infection.

In an exemplary embodiment, the RFP-RSV of the present disclosure may be prepared by mutating or modifying a part of the sequence of the fusion peptide of the RSV F protein.

The present disclosure is also directed to providing a soluble RSV F polypeptide, a nucleic acid molecule and/or a composition for inducing immunogenicity, and a use of the soluble RSV F protein for inducing immune response in an animal and human body, particularly a sue as a vaccine. The present disclosure also includes, as a specific use as a vaccine, a step of administering an effective amount of a nucleic acid molecule encoding the RSV F polypeptide, a vector including the nucleic acid molecule and/or a polypeptide transcribed from the nucleic acid molecule to a subject. In a specific aspect, the present disclosure relates to a method for inducing a neutralizing anti-respiratory syncytial virus (RSV) F protein antibody in a subject, which includes a step of administering an effective amount of a nucleic acid molecule encoding the RSV F polypeptide, a vector including the nucleic acid molecule and/or a polypeptide transcribed from the nucleic acid molecule to a subject.

In an exemplary embodiment, one or more hydrophobic amino acid at positions 137-145 of the amino acid sequence of SEQ ID NO: 2 may be substituted with a hydrophilic amino acid. More specifically, the RSV F protein of SEQ ID NO: 2 may have mutation wherein one or more hydrophobic amino acid of the fusion peptide is substituted with a hydrophilic. Further more specifically, in an exemplary embodiment of the present disclosure, the hydrophobic amino acids of the FLGFLLGVG (SEQ ID NO: 104) sequence at positions 137-145 of SEQ ID NO: 2 may be substituted with A to give AAGAAAGAG (SEQ ID NO: 95) and the modified fusion protein (SEQ ID NO: 3, FP1) may be linked with a polymerization domain derived form a heterologous protein.

In an exemplary embodiment, one or more polar amino acid at positions 137-145 of the amino acid sequence of SEQ ID NO: 2 137-145 may be substituted with a nonpolar amino acid. More specifically, the RSV F protein of SEQ ID NO: 2 may have mutation wherein a polar region of the fusion peptide is modified with a nonpolar side chain. Further more specifically, a fusion protein with the FLGFLLGVG sequence at positions 137-145 of SEQ ID NO: 2 modified to QNGQNNGSG (SEQ ID NO: 96) (FP3) may be linked with a polymerization domain derived form a heterologous protein.

In another exemplary embodiment, a fusion protein with the FLGFLLGVG (SEQ ID NO: 104) sequence at positions 137-145 of SEQ ID NO: 2 modified to NSGNSSGGG (SEQ ID NO: 97) (FP4) may be linked with a polymerization domain derived form a heterologous protein.

In another exemplary embodiment, a fusion protein with the FLGFLLGVG (SEQ ID NO: 104) sequence at positions 137-145 of SEQ ID NO: 2 modified to TLSKKRKRR (SEQ ID NO: 98) (FP6) may be linked with a polymerization domain derived form a heterologous protein.

The polymerization domain derived a heterologous protein may function as an immunogen when linked to the fusion protein. It may improve the stability of the protein structure and may advantageously induce a neutralizing antibody through trimerization.

Although mutation may occur at the amino acid sequence of positions 137-145 of SEQ ID NO: 2, the function and effect of the protein may vary greatly depending on the substitution, deletion or insertion of the amino acid constituting the protein as well known to those skilled in the art.

In another exemplary embodiment of the present disclosure, further mutation that stabilizes the F1 domain of the wild-type RSV F protein may be included. The further mutation related with stabilization includes at least one selected from a group consisting of (a)-(g) on the basis of SEQ ID NO: 2:

(a) substation of amino acid residue at position 140;
(b) substation of amino acid residue at position 163;
(c) substation of amino acid residue at position 179;
(d) substation of amino acid residue at position 188;
(e) substation of amino acid residue at position 189;
(f) substation of amino acid residue at position 487; and
(g) substation of amino acid residue at position 505.

More specifically, the RSV fusion protein of the present disclosure may have, on the basis of SEQ ID NO: 2, one or more amino acid substitution selected from a group consisting of:

(a) substation of amino acid residue F with W at position 140 (SEQ ID NO: 7);
(b) substation of amino acid residue E with Q at position 163 (SEQ ID NO: 8);
(c) substation of amino acid residue V with L at position 179 (SEQ ID NO: 9);
(d) substation of amino acid residue L with Q at position 188 (SEQ ID NO: 10);
(e) substation of amino acid residue T with L at position 189 (SEQ ID NO: 11);
(f) substation of amino acid residue E with L at position 487 (SEQ ID NO: 12); and
(g) substation of amino acid residue F with W at position 505 (SEQ ID NO: 13).

The fusion protein may be linked to a polymerization domain derived from a heterologous protein.

In another exemplary embodiment, the fusion protein may be one wherein,
the amino acid corresponding to position 140 of SEQ ID NO: 2 is substituted with the amino acid W, and the amino acid corresponding to position 163 is substituted with the amino acid Q (SEQ ID NO: 14);
the amino acid corresponding to position 140 of SEQ ID NO: 2 is substituted with the amino acid W, the amino acid corresponding to position 163 is substituted with the amino acid Q, the amino acid corresponding to position 188 is substituted with the amino acid Q, and the amino acid corresponding to position 189 is substituted with the amino acid L (SEQ ID NO: 15);
the amino acid corresponding to position 488 of SEQ ID NO: 2 is substituted with the amino acid W, and the amino acid corresponding to position 163 is substituted with the amino acid Q (SEQ ID NO: 16);
the amino acid corresponding to position 488 of SEQ ID NO: 2 is substituted with the amino acid W, and the amino acid corresponding to position 179 is substituted with the amino acid L (SEQ ID NO: 17);
the amino acid corresponding to position 140 of SEQ ID NO: 2 is substituted with the amino acid W, and the amino acid corresponding to position 505 is substituted with the amino acid W (SEQ ID NO: 18);
the amino acid corresponding to position 487 of SEQ ID NO: 2 is substituted with the amino acid L, and the amino acid corresponding to position 505 is substituted with the amino acid W (SEQ ID NO: 19);
the amino acid corresponding to position 163 of SEQ ID NO: 2 is substituted with the amino acid Q, and the amino acid corresponding to position 505 is substituted with the amino acid W (SEQ ID NO: 20);
the amino acid corresponding to position 188 of SEQ ID NO: 2 is substituted with the amino acid Q, the amino acid corresponding to position 189 is substituted with the amino acid L, and the amino acid corresponding to position 505 is substituted with the amino acid W (SEQ ID NO: 21); or
the amino acid corresponding to position 163 of SEQ ID NO: 2 is substituted with the amino acid Q, and the amino acid corresponding to position 487 is substituted with the amino acid L (SEQ ID NO: 22).

In an exemplary embodiment, the present disclosure provides an immunogenic composition and/or a vaccine, which contains a recombinant fusion protein of RSV wherein the RSV F protein is linked to a 'polymerization domain derived from a 'heterologous protein'.

The wild-type respiratory syncytial virus fusion protein may be selected from the F protein of an RSV A strain, an RSV B strain, an HRSV A strain, an HRSV B strain, an BRSV strain or an avian RSV strain or any variant thereof. In a specific exemplary embodiment, the wild-type F protein polypeptide may be an F protein represented by SEQ ID NO: 1, and an F protein which has sequence identity of 80% or higher to SEQ ID NO: 1 may also be included in the wild-type RSV of the present disclosure. Numerous additional examples of F protein polypeptides from other RSV strains are disclosed in WO/2008/114149 (which is incorporated herein by reference in its entirety). Additional variants can arise through genetic drift, or can be produced artificially using site-directed or random mutagenesis or by recombination of two or more preexisting variants.

In an exemplary embodiment of the present disclosure, the sF protein may be provided as a recombinant fusion protein (F protein) RSV as being linked to a polymerization domain derived from a heterologous protein at the C-terminal.

The polymerization domain derived a heterologous protein may be a polypeptide, and the polypeptide may be a bacteriophage T4 fibritin foldon domain polypeptide having SEQ ID NO: 23.

The foldon domain may be particularly advantageous for trimerization of the sF protein of the present disclosure, and may be excellent in inducing a neutralizing antibody.

The fusion protein to which the polymerization domain derived from a heterologous protein is linked, e.g., an sF protein, may have one or more amino acid sequence selected from SEQ ID NOS: 3-22, specifically an amino acid sequence of SEQ ID NO: 5. The amino acid of SEQ ID NO: 5 may be named FP4. The FP4 exhibits excellent stability and superior neutralizing antibody-inducing ability when a foldon domain or a foldon-flagellin D1 domain is bound.

In another exemplary embodiment, a recombinant D1 domain polypeptide of the flagellin protein having SEQ ID NO: 24 may be further linked at the C-terminal of the bacteriophage T4 fibritin foldon domain polypeptide having SEQ ID NO: 23. Through this, more improved neutralizing antibody induction may be expected.

In another exemplary embodiment, the RFP-RSV may have the C-terminal of the fusion protein (sF protein) linked to the N-terminal of the polymerization domain derived from a heterologous protein, and the linkage between the fusion protein and the polymerization domain may be covalent bonding by a linker. The linker may have an amino acid sequence of KLSG (SEQ ID NO: 99), and may be called a KLSG (SEQ ID NO: 99) linker. In an exemplary embodiment, the RFP-RSV may have the C-terminal of the KLSG (SEQ ID NO: 99) linker covalently bonded to the N-terminal of the bacteriophage T4 fibritin foldon domain polypeptide having SEQ ID NO: 23. In an exemplary embodiment, the present disclosure may provide RFP-RSV having an amino acid sequence selected from SEQ ID NOS: 28-48.

In another exemplary embodiment, the RFP-RSV may have the C-terminal of the bacteriophage T4 fibritin foldon domain polypeptide having SEQ ID NO: 23 linked to the recombinant D1 domain polypeptide of the flagellin protein having SEQ ID NO: 24 by a GGGS (SEQ ID NO: 100) linker having the amino acid sequence of GGGS (SEQ ID NO: 100). In an exemplary embodiment, the recombinant fusion protein of respiratory syncytial virus may have the C-terminal of the fusion protein (F protein) linked to the N-terminal of the bacteriophage T4 fibritin foldon domain polypeptide having SEQ ID NO: 23 by a KLSG (SEQ ID NO: 99) linker, and the C-terminal of the bacteriophage T4 fibritin foldon domain polypeptide having SEQ ID NO: 23 linked to the N-terminal of the recombinant D1 domain polypeptide of the flagellin protein having SEQ ID NO: 24 by a GGGS (SEQ ID NO: 100) linker. The RFP-RSV may be an RFP-RSV having an amino acid sequence selected from SEQ ID NOS: 49-69.

In an exemplary embodiment, the RFP-RSV may have the C-terminal of the sF protein linked to a polymerization domain derived from a heterologous protein by a linker, and the linkage by the linker may be covalent bonding.

In an exemplary embodiment, the recombinant fusion protein may include two or more linkers and two or more polymerization domains derived from heterologous proteins.

For example, the recombinant fusion protein may be roughly described as follows. However, the SK-FP4 described below is only an example of the sF protein provided for illustrative purpose, and the present disclosure is not limited thereto. In addition, the linker 1 and the linker 2 may be the same or different, and the polymerization domain derived from a heterologous protein 1 and 2 may also be the same or different.

(sF protein)-(linker 1)-(polymerization domain derived from a heterologous protein 1)
(sF protein)-(linker 2)-(polymerization domain derived from a heterologous protein 2)
(sF protein)-(linker 1)-(polymerization domain derived from a heterologous protein 1)-(linker 3)-(polymerization domain derived from a heterologous protein 2)

In another exemplary embodiment, the present disclosure may include the following recombinant fusion proteins.

(sF protein)-(linker 1)-(polymerization domain derived from a heterologous protein 1)
(sF protein)-(linker 2)-(adjuvant domain derived from a heterologous protein)
(sF protein)-(linker 1)-(polymerization domain derived from a heterologous protein 1)-(linker 2)-(adjuvant domain derived from a heterologous protein)

For example, the adjuvant domain derived from a heterologous protein may include the flagellin protein and the D1 domain of the flagellin protein.

In an exemplary embodiment of the present disclosure, the linker 1 may be a KLSG linker, the linker 2 may be a KLGGGS (SEQ ID NO: 101) linker, and the linker 3 may be a GGGS (SEQ ID NO: 100) linker. Specifically, the C-terminal of the KLSG (SEQ ID NO: 99) linker may be linked to the N-terminal of the foldon domain, and the C-terminal of the KLGGGS (SEQ ID NO: 101) linker may be linked to the D1 domain of flagellin (specifically, the recombinant D1 domain of flagellin). Specifically, the C-terminal of the foldon domain and the N-terminal of the D1 domain of flagellin may be linked by a GGGS (SEQ ID NO: 100) linker.

In an exemplary embodiment, the recombinant fusion protein may be provided in the form wherein a KLSG (SEQ ID NO: 99) linker or a KLGGGS (SEQ ID NO: 101) linker is bound to the C-terminal of the sF protein. Specifically, the KLSG (SEQ ID NO: 99) linker may link the sF protein with the foldon domain. The linkage may be formed by covalent bonding. The C-terminal of the sF protein may be linked to the N-terminal of the KLSG (SEQ ID NO: 99) linker, and the C-terminal of the KLSG (SEQ ID NO: 99) linker may be linked to the N-terminal of the foldon domain. Specifically, the KLGGGS (SEQ ID NO: 101) linker may link the sF protein and the D1 domain of flagellin (specifically, the recombinant D1 domain of flagellin). The linkage may be formed by covalent bonding. The C-terminal of the sF protein may be linked to the N-terminal of the KLSG (SEQ ID NO: 99) linker, and the C-terminal of the KLSG (SEQ ID NO: 99) linker may be linked to the N-terminal of the D1 domain of flagellin (specifically, the recombinant D1 domain of flagellin).

In an exemplary embodiment, when the sF protein is linked to the polymerization domain derived from a heterologous protein by a linker in the recombinant fusion protein, the C-terminal of the linker having the amino acid sequence KLSG (SEQ ID NO: 99) may be covalently bonded to the N-terminal of the bacteriophage T4 fibritin foldon domain having SEQ ID NO: 23.

In another exemplary embodiment, the present disclosure provides an RFP-RSV wherein the recombinant D1 domain polypeptide of the flagellin protein having SEQ ID NO: 24 is linked to the C-terminal of the fusion protein (F protein) with the transmembrane domain at amino acids 525-574 of the wild-type respiratory syncytial virus (RSV) fusion protein (F protein) of SEQ ID NO: 1 deleted. The amino acid sequence of the fusion protein (F protein) with the transmembrane domain at amino acids 525-574 of the wild-type respiratory syncytial virus (RSV) fusion protein (F protein) of SEQ ID NO: 1 deleted may be represented by SEQ ID NO: 2. In another exemplary embodiment, the present disclosure may provide an RFP-RSV wherein the C-terminal of an amino acid sequence represented by SEQ ID NOS: 3-22 is covalent bonded to a recombinant D1 domain polypeptide of the flagellin protein (SEQ ID NO: 24) by a KLGGGS (SEQ ID NO: 101) linker. The RFP-RSV may be represented by an amino acid sequence selected from SEQ ID NOS: 70-90.

In another exemplary embodiment, the present disclosure may provide a nucleic acid encoding the RFP-RSV. The recombinant fusion protein may be used as an RSV antigen, and the present disclosure may provide a recombinant nucleic acid encoding the antigen.

In a specific exemplary embodiment, the recombinant nucleic acid is codon-optimized to be expressed in a selected prokaryotic or eukaryotic host cell. As a non-limiting example, the recombinant fusion protein may have an amino acid sequence selected from SEQ ID NOS: 28-90. The nucleic acid may be introduced into a prokaryotic or eukaryotic vector.

The recombinant F protein of RSV of the present disclosure is useful for preparing a composition for inducing immune response, which provides immunity or substantial immunity against an infectious agent. Accordingly, in an exemplary embodiment, the present disclosure provides a method for inducing immunity against infection or the symptoms of a disease, which includes a step of administering an effective dose of the recombinant RSV F protein at least once.

In another exemplary embodiment, the present disclosure provides a method for inducing substantial immunity against infection or the symptoms of a disease, which includes a step of administering an effective dose of the recombinant RSV F protein at least once.

The composition of the present disclosure may induce substantial immunity when administered to a vertebrate (e.g., human).

Production of RSV F Gene-Introduced Recombinant Baculovirus

The expression product encoded by the nucleic acid of the present disclosure may be produced by being cloned into a recombinant viral vector.

The recombinant viral vector may be, for example, a phage, a plasmid, a virus or a retroviral vector. Specifically, a viral vector may be used.

In an exemplary embodiment, the vector may be a recombinant baculoviral vector. The construct and/or vector encoding the gene should be operably linked to an appropriate promoter such as the AcMNPV polyhedrin promoter (or other baculovirus), phage lambda (PL) promoter, *E. coli* lac, phoA and tac promoter. Specifically, it may be overexpressed by the polyhedrin promoter.

The expression construct will further include sites for initiation and termination of transcription and, in the transcribed region, a ribosome-binding site for translation. The coding portion of the transcript expressed by the construct will specifically include a translation initiation codon at the beginning and a termination codon appropriately positioned at the end of the polypeptide to be translated. The expression vector will specifically include at least one selectable marker. The marker includes dihydrofolate reductase, G418 or neomycin resistance gene for eukaryotic cell culture, and tetracycline, kanamycin or ampicillin resistance gene for culture of *E. coli* and other bacteria. Specifically, the vector may be one or more viral vector selected from a group consisting of baculovirus (e.g., *Autographa californica* nucleopolyhedrovirus), adenovirus (e.g., canine adenovirus), hepadnavirus (e.g., avihepadnavirus), vacciniavirus (e.g., modified vaccinia Ankara virus) and parvovirus (e.g., autonomous parvovirus). The baculovirus may include *Autographa californica* nucleopolyhedrovirus or a modified virus strain thereof, and *Bombyx mori* nucleopolyhedrovirus or a modified virus strain thereof. Also, a bacterial vector may be used. Exemplary bacterial vectors include pQE70, pQE60 and pQE-9, pBluescript vectors, and Phagescript vectors, pNH8A, pNH16a, pNH18A, pNH46A, ptrc99a, pKK223-3, pKK233-3, pDR540 and pRIT5. Eukaryotic vectors may include pFastBac1 pWINEO, pSV2CAT, pOG44, pXT1, pSG, pSVK3, pBPV, pMSG, pSVL, etc.

The recombinant vector described above may be used for transfection, infection or transformation, and may express proteins in eukaryotic cells and/or prokaryotic cells. Eukaryotic host cells may include yeast, insect, avian, plant, *Caenorhabditis elegans* (or nematode) and mammal host cells. Non-limiting examples of insect cells are *Spodoptera frugiperda* (Sf) cells such as Sf9 and Sf21, *Trichoplusia ni* cells such as High Five cells, and *Drosophila* S2 cells. Examples of fungal (including yeast) host cells include *S. cerevisiae, Kluyveromyces lactis* (*K. lactis*), *C. albicans, C. glabrata, Aspergillus nidulans, Schizosaccharomyces pombe* (*S. pombe*), *Pichia pastoris* and *Yarrowia lipolytica*. Examples of mammalian cells are 293 cells (human embryonic kidney lineage), CHO cells (Chinese hamster ovary cell lineage), Vero cells (African green monkey lineage), MRC cells (human lung fibroblast cell lineage) and MDCK cells (Madin-Darby canine kidney cell lineage). African clawed frog (*Xenopus laevis*) oocytes or other cells of amphibian origin may also be used. Prokaryotic host cells include bacteria cells, e.g., *E. coli, Bacillus subtilis* (*B. subtilis*) and mycobacterial cells.

Pharmaceutical or Vaccine Preparation and Administration

In an exemplary embodiment, the present disclosure provides a vaccine or a vaccine composition for preventing RSV, which contains the recombinant fusion protein according to various exemplary embodiments of the present disclosure. Specifically, the RFP-RSV contained in the vaccine composition may be one wherein the post-fusion fusion protein is linked to the polymerization domain or the flagellin protein recombinant D1 domain.

The vaccine may contain an adjuvant. For example, the adjuvants described in Korean Patent Publication No. 10-2011-0112328 may be used without limitation. Specifically, the vaccine of the present disclosure may contain an aluminum adjuvant, more specifically an aluminum hydroxide adjuvant.

The vaccine composition of the present disclosure may contain any pharmaceutical substance which does not cause in itself harmful immune response in a vertebrate to which the composition is administered, and may contain a pharmaceutically acceptable carrier including any appropriate diluent or excipient that can be administered together with the recombinant F protein without excessive toxicity. The term "pharmaceutically acceptable" means being listed in the US Pharmacopeia, European Pharmacopeia or other generally recognized pharmacopoeias for use in vertebrates, more particularly in human. The RSV F antigen of the present disclosure is administered in an effective amount (as defined above) which is sufficient to induce immune response against one or more strain of the RSV virus. The composition may be used as a vaccine and/or immunogenic composition for inducing protective immune response in vertebrate.

In one non-limiting exemplary embodiment, the concentration of the recombinant F protein of RSV contained in the vaccine is at least about 10 μg/mL, about 20 μg/mL, about 30 μg/mL, about 40 μg/mL, about 50 μg/mL, about 60 μg/mL, about 100 μg/mL, about 200 μg/mL, or about 500 μg/mL. In a specific exemplary embodiment, the concentration of the immunogen is from about 10 μg/mL to about 1 mg/mL, from about 20 μg/mL to about 500 μg/mL, from about 30 μg/mL to about 100 μg/mL, or from about 30 μg/mL to about 50 μg/mL. In another exemplary embodiment, the concentration of the immunogen may be 10-200 μg/mL.

The vaccine or immunogen composition of the present disclosure may be administered to an animal to induce immune response against RSV. In an exemplary embodiment, the animal is human. Usually, the administration dosage may be adjusted within the above-described range on the basis of, for example, age, physical condition, body weight, diet, administration time and other clinical factors. Accordingly, the present disclosure includes a method for preparing a vaccine or immunogen composition which induces substantial immunity against infection or at least one symptom thereof in a subject, which includes a step of adding an effective amount of the immunogen. Although it is desired that substantial immunity is induced with a single dose, additional dosages can be administered via the same or different route to achieve the desired effect. For example, in neonates and infants, multiple administrations may be required to elicit sufficient level of immunity. The administration can continue with intervals throughout childhood if it is necessary to maintain sufficient level of protection against infection. In an exemplary embodiment, a method for inducing substantial immunity against viral infection or at least one symptom thereof in a subject includes a step of administering at least one effective dose of the RSV recombinant F protein, or a fragment or an aggregate thereof. The method for administering the vaccine and/or immunogen preparation includes parenteral (e.g., intradermal, intramuscular, intravenous or subcutaneous) administration, epidural administration and mucosal (e.g., intranasal, oral, pulmonary or suppository) administration, although not being limited thereto. In a specific exemplary embodiment, the composition is administered intramuscularly, intravenously, subcutaneously, orally or intradermally. The composition may be administered via any convenient route, for example, by infusion, bolus injection, absorption through epithelial or mucosal linings (e.g., oral, colonic, conjunctival, nasopharyngeal, oropharyngeal, vaginal, urethral, bladder or intestinal mucosa) and may be administered together with another biologically active agent. The administration can be systemic or local. The prophylactic vaccine preparation is administered systemically, e.g., by subcutaneous or intramuscular injection using a needle and a syringe, or a needle-less injection device. Alternatively, the vaccine formulation is administered intranasally as drops, large aerosol particles (greater than about 10 microns) or sprays into the upper respiratory tract. Although any of the above routes of delivery results in immune response, the intranasal administration confers the added benefit of eliciting mucosal immunity at the site of the entry of the virus. In another exemplary embodiment, the vaccine and/or immunogen preparation is administered to target mucosal tissues in order to elicit an immune response at the site of immunization. For example, mucosal tissues such as gut associated lymphoid tissue (GALT) can be targeted for immunization through oral administration of a compositions which contains an immunogenic adjuvant with specific mucosal targeting properties. Additional mucosal tissues can also be targeted, such as nasopharyngeal lymphoid tissue (NALT) and bronchial-associated lymphoid tissue (BALT).

As the preparation method of a vaccine containing the RSV recombinant F protein of the present disclosure, the administration method thereof and the route of administration, those described in Korean Patent Publication No. 10-2011-0112328 may be used without limitation.

The present disclosure may provide a medicine for treating or preventing respiratory syncytial viral infection, which contains the RSV recombinant fusion protein as an antigen.

The present disclosure provides a use of the RSV antigen for preparation of a medicine for preventing RSV infection.

The present disclosure provides a method for inducing immune response against RSV by administering the RSV recombinant respiratory syncytial virus antigen or a vaccine containing the antigen to a subject.

In another exemplary embodiment, the present disclosure provides a pharmaceutical pack or kit containing one or more container filled with one or more ingredient of the vaccine preparation of the present disclosure.

In another exemplary embodiment, the present disclosure provides a method for preparing a vaccine or an antigen composition for inducing immunity against infection or at least one symptom thereof in a mammal, which includes a step of adding an effective dose of RFP-RSV to the preparation. In a specific exemplary embodiment, the infection is RSV infection.

The RFP-RSV of the present disclosure is useful for preparing a composition which induces immune response and provides immunity or substantial immunity against an infectious agent. Accordingly, in an exemplary embodiment, the present disclosure provides a method for inducing immunity against infection or at least one symptom thereof in a subject, which includes a step of administering at least one effective dose of RFP-RSV.

In another exemplary embodiment, the present disclosure provides a method for inducing substantial immunity against RSV viral infection or at least one symptom thereof in a subject by administering at least one effective dose of RFP-RSV.

The composition of the present disclosure may induce substantial immunity in a vertebrate (e.g., human) when administered to the vertebrate. Accordingly, in an exemplary embodiment, the present disclosure provides a method for inducing substantial immunity against RSV viral infection or at least one symptom thereof in a subject, which includes a step of administering at least one effective dose of RFP-RSV.

In another exemplary embodiment, the present disclosure provides the recombinant fusion protein of respiratory syncytial virus of the present disclosure for use as a vaccine for prevention of infection by respiratory syncytial virus.

Advantageous Effects

The present disclosure provides an immunogenic composition for prevention of RSV infection.

The present disclosure may achieve further improved RSV F protein expression in a host cell than the wild-type RSV F protein through recombination of the RSV F protein.

The RSV recombinant F protein of the present disclosure may act as a superior RSV immunogen.

The RSV recombinant F protein of the present disclosure may provide excellent neutralizing antibody titer.

The present disclosure may provide an RSV F protein which is stable and soluble.

The present disclosure may provide an RSV recombinant F protein antigen having excellent safety.

The present disclosure may provide an RSV antigen and a vaccine having high neutralizing antibody titer.

DESCRIPTION OF DRAWINGS

FIG. 9 shows a result of analyzing the RSV A2 neutralizing antibody titer of mouse antiserum.

MODE FOR DISCLOSURE

Hereinafter, the present disclosure will be described in detail through examples, etc. in order to help understanding. However, the examples according to the present disclosure may be changed into various other forms and it should not be interpreted that the scope of the present disclosure is limited by the examples. The examples of the present disclosure are provided such that the description of the present disclosure is more complete to those having ordinary knowledge in the art.

1. Preparation of RSV Recombinant F Protein

Preparation of sF Protein (1) In order to obtain an RSV recombinant F protein which is stable and soluble, wild-type RSV was prepared as follows. It is well known to those skilled in the art that the following mutations are applied to all RSV subtypes including wild-type RSV-A2, RSVB and RSV-A long. The wild-type RSV F protein of RSV-B GenBank Accession No. AEQ63641.1 was mutated.

(2) A transmembrane domain of the wild-type F protein was removed. The wild-type F protein with the transmembrane domain removed was named SK-Seq 1_dTM and was represented by SEQ ID NO: 2. Then, the amino acid sequence of the fusion peptide, which corresponds to the positions 137-145 of SEQ ID NO: 2, was changed. SK-FP4 of SEQ ID NO: 5 (an example of sF protein) was obtained by substituting the amino acid sequence FLGFLLGVG (SEQ ID NO: 104) at the positions with NSGNSSGGG (SEQ ID NO: 97).

Preparation of Polymerization Domain Derived from Heterologous Protein

A domain which is derived from a heterologous protein and can help maintenance of the trimer form of the F protein was introduced to the C-terminal of SK-PF4 of SEQ ID NO: 1, which is one of sF proteins.

(1) Preparation of Foldon Domain

A foldon domain of the fibritin protein of bacteriophage T4 was prepared.

The domain was represented by SEQ ID NO: 23.

(2) Preparation of Recombinant D1 Domain of Flagellin

The flagellin protein is a building block of the flagellar filament and is encoded by the fliC gene. The flagellin protein of *Salmonella enterica* was used. The flagellin protein which is encoded by the FliC gene possessed by the serotype group D (Dublin) of *Salmonella enterica* ssp. *enterica* was used for experiment.

The recombinant D1 domain of flagellin to be fused with FP4 was designed by linking the amino acid sequences 54-176 and 413-454 of the D1 domain of the FliC gene possessed by the serotype group D (Dublin) of *Salmonella enterica* ssp. *enterica* with a linker G.

The domain was named SK_fla and was represented by SEQ ID NO: 24.

(3) Preparation of Linker

A linker that can be link the domain to the C-terminal of SK-FP4 was prepared.

Figure 1:
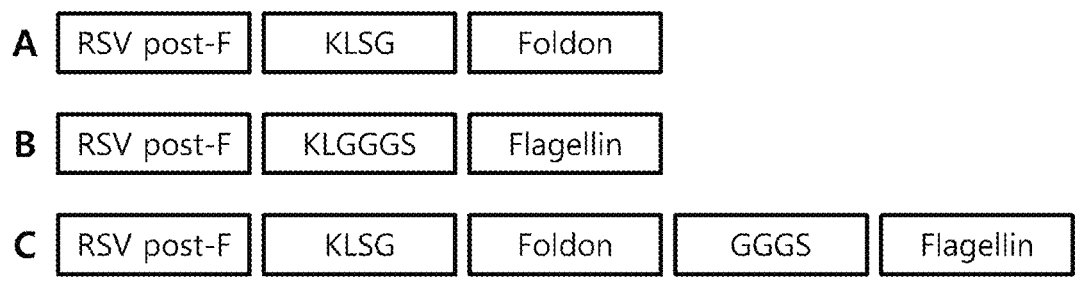
FIG. 1 schematically shows the concept of the present disclosure including the linkers KLSG (SEQ ID NO: 99), GGGS (SEQ ID NO: 100), and KLGGGS (SEQ ID NO: 101).
Figure 2:
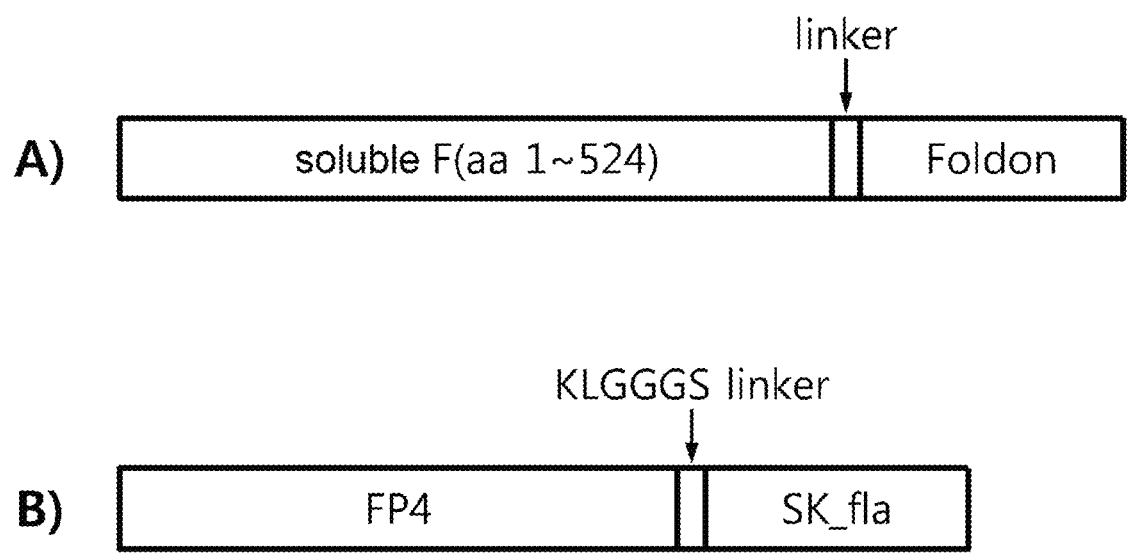
FIG. 2A) schematically shows foldon linked to the C-terminal of SK-FP4 by a KLSG (SEQ ID NO: 99) linker, and B) schematically shows SK_fla linked to the C-terminal of SK-FP4 by a KLGGGS (SEQ ID NO: 101) linker.

Foldon was linked to the C-terminal of SK-FP4 with a KLSG (SEQ ID NO: 99) linker (see FIG. 2A).

Figure 3:
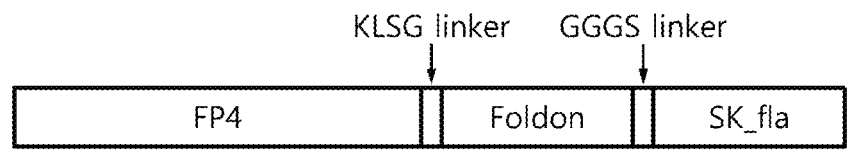
FIG. 3 schematically shows foldon and SK_fla linked to the C-terminal of SK-FP4. The sequence of linkage is F4-KLSG-foldon-GGGS-flagellin including the KLSG (SEQ ID NO: 99) linker and the GGGS (SEQ ID NO: 100) linker.

SK_fla was linked to the C-terminal of foldon with a KLGGGS (SEQ ID NO: 101) linker (see FIG. 2B). Then, foldon and SK_fla were linked with a GGGS (SEQ ID NO: 100) linker (see FIG. 3).

Designing of Recombinant Polymerization Domain-Bound Fusion Protein

A recombinant fusion protein of RSV (RFP-RSV) was designed as follows.

Foldon and/or SK_fla was linked to the sF protein by a linker. As a result, RFP-RSVs having SEQ ID NOS: 28-90 were obtained.

Among them, FP4 having SEQ ID NO: 5 was designed as follows.

(1) Designing of FP4-Foldon Fusion Protein

Foldon was linked to the C-terminal of FP4 by a KLSG (SEQ ID NO: 99) linker (see SEQ ID NO: 31).

(2) Designing of FP4-Flagellin Fusion Protein

SK_fla was linked to the C-terminal of FP4 by a KLGGGS (SEQ ID NO: 101) linker (see SEQ ID NO: 73).

(3) Designing of FP4-Foldon-Flagellin Fusion Protein

After fusing foldon to the C-terminal of FP4 with a KLSG (SEQ ID NO: 99) linker, flagellin was fused with a GGGS (SEQ ID NO: 100) linker (see SEQ ID NO: 52).

2. Production of Recombinant Baculovirus (1) Preparation of Recombinant Baculovirus For easy differentiation of the designed recombinant fusion protein, the DNA sequence of a gene encoding the recombinant fusion protein was optimized. A DNA sequence having SEQ ID NO: 91, a DNA sequence having SEQ ID NO: 92 and a DNA sequence having SEQ ID NO: 93 were cloned respectively into the pFastBac™1 transfer vector.

Then, recombinant baculovirus (rBV_FP4-foldon, rBV_FP4-flagellin, and rBV_FP4-foldon-flagellin) was prepared using the recombinant pFastBac™1 and the Bac-to-bac® baculovirus expression system (Invitrogen).

Table 1 shows the plaque titer of the recombinant baculovirus stocks.

TABLE 1

| Recombinant baculovirus | P0 titration | P1 titration | P2 titration |
|---|---|---|---|
| rBV_FP4-foldon | $8.8 \times 10^5$ pfu/ml | $5.8 \times 10^7$ pfu/ml | $1.2 \times 10^7$ pfu/ml |
| rBV_FP4-flagellin | $3.0 \times 10^6$ pfu/ml | $3.4 \times 10^7$ pfu/ml | $1.0 \times 10^7$ pfu/ml |
| rBV_FP4-foldon-flagellin | $1.1 \times 10^6$ pfu/ml | $1.1 \times 10^8$ pfu/ml | $1.6 \times 10^8$ pfu/ml |

Figure 4:
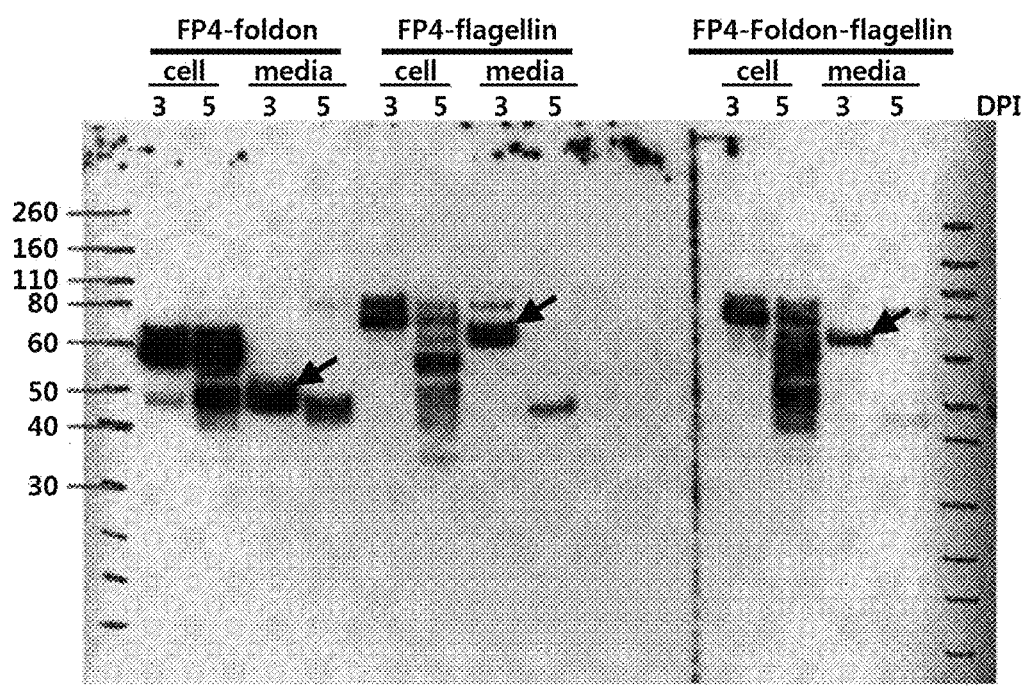
FIG. 4 shows the expression of the recombinant F protein of the present disclosure.

(2) Expression of FP4-Foldon, FP4-Flagellin and FP4-Foldon-Flagellin Fusion Proteins Sf9 insect cells were cultured at 27° C. using the insect-XPRESS™ medium (Lonza). When the cell concentration reached $1.5 \times 10^6$ cells/mL, the cells were infected with the recombinant baculovirus expressing the FP4-foldon, FP4-flagellin or FP4-foldon-flagellin fusion protein at MOI of 0.5. On days 3 and 5 after the infection, the expression of the fusion protein in the medium and the cells was analyzed by western blot under reducing condition (detection was made using the mouse monoclonal antibody 2F7). Protein expression was confirmed in both the cells and the medium, and protein degradation was observed with time. The result is shown in FIG. 4.

3. Purification of Protein (1) Purification of FP4-Foldon Protein

Sf9 cells were cultured in a 1-L spinner flask. When the cell concentration reached $1.5 \times 10^6$ cells/mL, the Sf9 cells were infected with FP4-foldon rBV P1 at MOI of 0.5, and the medium was recovered 3 days later through centrifugation 6000 g for 15 minutes. TMAE anion exchange chromatography was conducted through column equilibration with 50 mM Tris (pH 8). After loading the prepared culture medium into the column, the flow-through sample was recovered. The flow-through sample was buffer-exchanged and concentrated by UF/DF using a buffer (20 mM Tris, 150 mM NaCl, pH 7.4). A Lentil Lectins column was equilibrated by applying a binding buffer (20 mM Tris, 0.5 M NaCl, 1 mM $CaCl_2$), 1 mM $MnCl_2$, pH 7.4). After adding 1 mM $MnCl_2$ and 1 mM $CaCl_2$, the sample was loaded into the column.

The protein was eluted by flowing an elution buffer (50 mM sodium phosphate, 100 mM NaCl, 0.5 M methyl-D-mannopyranoside, pH 6.8). The recovered sample was buffer-exchanged and concentrated by UF/DF using PBS. 0.1% Tween-80 was added to the finally recovered protein sample.

(2) The FP4-flagellin and FP4-foldon-flagellin proteins were also purified by the same method. But, unlike in (1), TMAE anion exchange chromatography was conducted through column equilibration with 50 mM sodium phosphate (pH 6.7).

Figure 5:
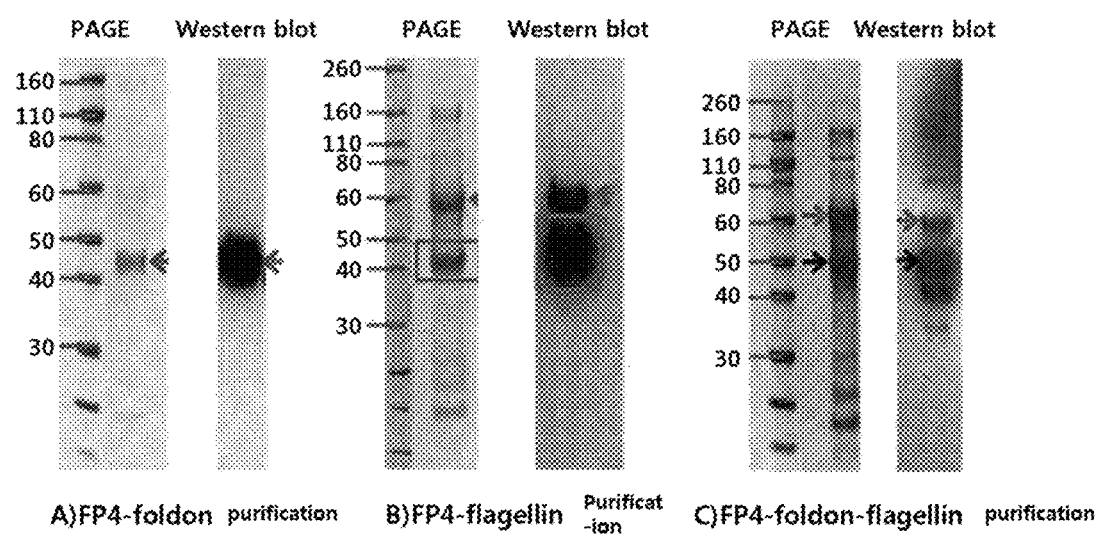
FIG. 5 shows a result of purifying the recombinant F protein of the present disclosure.

The result of protein purification is shown in FIG. 5.

4. Analysis of Protein Structure by Electron Microscopy

The purified protein sample was mounted on a disc and negative staining was performed. The protein was observed with an electronic microscope.

Figure 6:
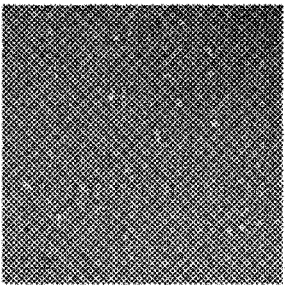
FIG. 6 shows a result of analyzing FP4 and FP4-foldon and FP4-flagellin fusion proteins by TEM.
Figure 7:
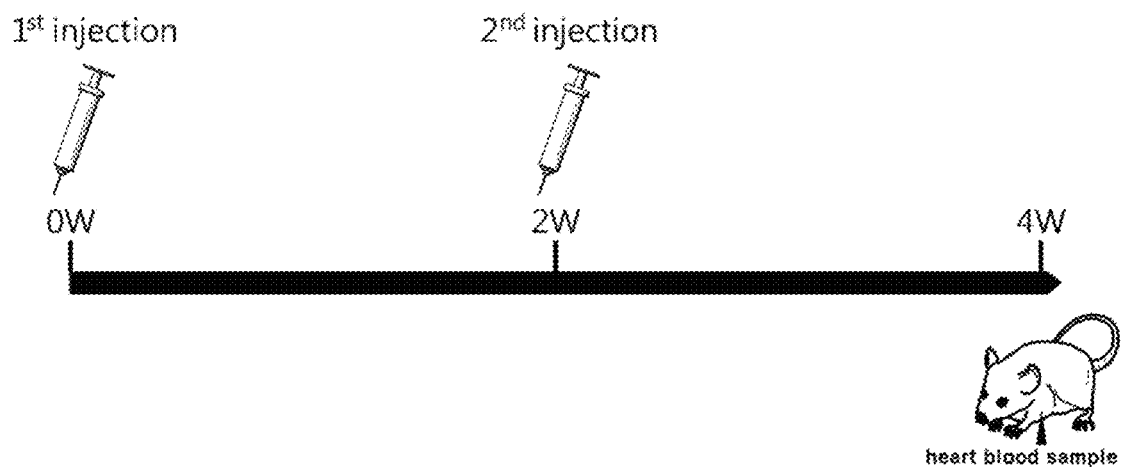
FIG. 7 shows a schedule of administration of the recombinant F protein of the present disclosure and blood sampling.

The result is shown in FIG. 6. The soluble FP4 not fused with foldon looked smaller and thinner than the FP4-foldon fusion protein as a whole. The FP4-foldon had a lollipop-like shape.

5. Test of Immunogenicity (1) Inoculation of FP4-Foldon, FP4-Flagellin and FP4-Foldon-Flagellin Fusion Proteins to Mouse and Gathering of Serum The purified FP4-foldon, FP4-flagellin or FP4-foldon-flagellin fusion protein and FP4 were formulated with aluminum hydroxide. The prepared formulation was administered 2 times to 6-week-old female Balb/c mouse via IM route at 30 μg/mouse with a 2-week interval. Details are given in Table 2.

TABLE 2

| Groups | Description | Antigen content | Aluminum hydroxide content | Mouse n |
|---|---|---|---|---|
| Group 1 | FP4-foldon | 30 μg | 200 μg | 5 |
| Group 2 | FP4-flagellin | 30 μg | 200 μg | 5 |
| Group 3 | FP4-foldon-flagellin | 30 μg | 200 μg | 5 |
| Group 4 | FP4 | 30 μg | 200 μg | 5 |
| Group 5 | PBS | 0 μg | 200 μg | 5 |

(2) Analysis of F Protein-Specific Antibody Titer of Mouse Antiserum

The soluble F-specific IgG antibody titer of mouse antiserum was measured by indirect ELISA. After coating the soluble F protein on the bottom of a 96-well plate, with 200 ng per well, and binding 4-fold serially diluted antiserum, anti-mouse IgG-HRP antibody was bound thereto and OD value was measured after adding TMB substrate. After analyzing the reaction curve for each mouse with a 4-parameter logistic model, $EC_{50}$ antibody titer and GMT antibody titer for 5 mice were calculated. The $EC_{50}$ antibody titer and GMT for soluble post-fusion F protein (post-F)-specific IgG are shown in Table 3 and FIG. 8.

TABLE 3

| Groups | Antigens | #1 | #2 | #3 | #4 | #5 | GMT |
|---|---|---|---|---|---|---|---|
| Group 1 | FP4-foldon | 3400 | 1345 | 2399 | 3099 | 3644 | 2622 |
| Group 2 | FP4-flagellin | 2264 | 1752 | 2413 | 1922 | 773 | 1701 |
| Group 3 | FP4-foldon + flagellin | 5812 | 6200 | 1780 | 4636 | 1826 | 3523 |
| Group 4 | FP4 | 3306 | 2946 | 1823 | 3398 | 985 | 2264 |
| Group 5 | PBS/alum | 72 | 50 | 11 | 130 | 79 | 53 |

Figure 8:
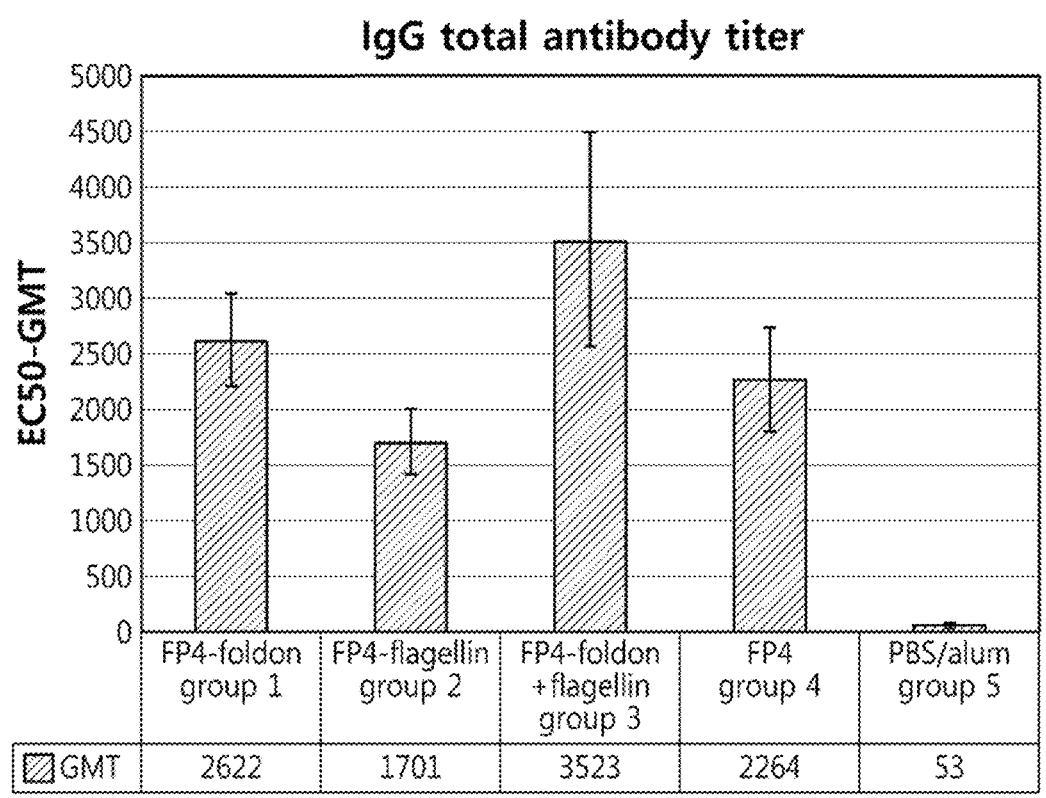
FIG. 8 shows a result of analyzing the soluble post-fusion F protein-specific IgG total antibody titer of mouse antiserum.

As can be seen from Table 3 and FIG. 8, Groups 1 and 3 showed increased total antibody titer as compared to FP4. Group 2 having only flagellin linked showed very low GMT as compared to Group 4 treated with FP4 alone. That is to say, it can be seen from the above result that total antibody titer was increased as the foldon trimerization domain was bound. Through this, it was confirmed that the recombinant fusion protein of the present disclosure can play an important role in all immune responses induced by antigens.

(3) Analysis of RSV Neutralizing Antibody Titer of Fusion Protein Mouse Antiserum A monolayer of Vero cells was cultured on a 24-well plate and infected with RSV A2 virus that had been pre-incubated with 2-fold serially diluted antiserum. Three days later, the infected cells were fixed and immunostained with palivizumab, and then immunofocus was counted. The number of immunofocus of each group depending on serum dilution factor is shown in Table 4. The average immunofocus of Group 5, which was inoculated with PBS-alum, was 67.6. The serum dilution factor ($ND_{50}$) at which the immunofocus was half, i.e., 33.8, was defined as neutralizing antibody titer. The focus forming unit and $ND_{50}$ depending on serum dilution factor are shown in Table 4 and FIG. 9.

TABLE 4

| Groups | Antigens | Serum dilution factor | | | | | | $ND_{50}$ |
| --- | --- | --- | --- | --- | --- | --- | --- | --- |
| | | 10 | 20 | 40 | 80 | 160 | 320 | |
| Group 1 | FP4-foldon | 28 | 37 | 45 | 46.5 | 64.5 | 68 | 18 |
| Group 2 | FP4-flagellin | 20 | 35.5 | 45 | 57 | 50 | 60 | 23 |
| Group 3 | FP4-foldon + flagellin | 11.5 | 23 | 32 | 46.5 | 63.5 | 56.5 | 47 |
| Group 4 | FP4 | 27.5 | 35 | 50.5 | 55.5 | 67.5 | 56.5 | 18.5 |
| Group 5 | PBS/alum | 60.5 | 68 | 59.5 | 65 | 78.5 | 74 | ND |

As can be seen from Group 3, the recombinant F protein wherein both foldon and flagellin proteins were linked resulted in remarkably increased neutralizing antibody production. The neutralizing antibody titer ratio of FP4-foldon-flagellin and FP4-foldon was 2.6, which means that the RSV neutralizing antibody titer was increased by 2.6 times through fusion with flagellin.

The neutralizing antibody titer ratio of FP4-foldon-flagellin and FP4-flagellin was 2.04, which means that the RSV neutralizing antibody titer was increased by 2.04 times through fusion with foldon.

INDUSTRIAL APPLICABILITY

The present disclosure may provide a vaccine against respiratory syncytial virus. The present disclosure may also provide a composition for preventing or treating respiratory syncytial virus infection.

What is claimed is:

1. A recombinant fusion protein (F protein) of respiratory syncytial virus (RSV), wherein:
a polymerization domain derived from a heterologous protein is linked at the C-terminus of a fusion protein (F protein) with the transmembrane domain of the wild-type respiratory syncytial virus (RSV) fusion protein (F protein) deleted;
the polymerization domain derived from a heterologous protein is a polypeptide, and the polypeptide is a bacteriophage T4 fibritin foldon domain polypeptide having SEQ ID NO: 23; and
the fusion protein (F protein) with the transmembrane domain of the wild-type respiratory syncytial virus (RSV) fusion protein (F protein) deleted has an amino acid sequence selected from SEQ ID NOS: 3-22.

2. The recombinant fusion protein of respiratory syncytial virus according to claim 1, wherein the recombinant fusion protein of respiratory syncytial virus further has a recombinant D1 domain polypeptide of the flagellin protein having SEQ ID NO: 24 linked to the C-terminus of the bacteriophage T4 fibritin foldon domain polypeptide having SEQ ID NO: 23.

3. The recombinant fusion protein of respiratory syncytial virus according to claim 1, wherein the recombinant fusion protein of respiratory syncytial virus has the N-terminus of the polymerization domain derived from a heterologous protein linked to the C-terminus of the fusion protein (F protein), and the fusion protein (F protein) and the polymerization domain derived from a heterologous protein are covalently bonded by a linker.

4. The recombinant fusion protein of respiratory syncytial virus according to claim 3, wherein the linker has the amino acid sequence of KLSG (SEQ ID NO: 99).

5. The recombinant fusion protein of respiratory syncytial virus according to claim 4, wherein the C-terminus of the KLSG (SEQ ID NO: 99) linker is covalently bonded to the N-terminus of the bacteriophage T4 fibritin foldon domain polypeptide having SEQ ID NO: 23.

6. The recombinant fusion protein of respiratory syncytial virus according to claim 5, wherein the recombinant fusion protein of respiratory syncytial virus has an amino acid sequence selected from SEQ ID NOS: 28-48.

7. The recombinant fusion protein of respiratory syncytial virus according to claim 2, wherein the C-terminus of the bacteriophage T4 fibritin foldon domain polypeptide having SEQ ID NO: 23 is linked to the recombinant D1 domain polypeptide of the flagellin protein having SEQ ID NO: 24 by a linker having the amino acid sequence of GGGS (SEQ ID NO: 100).

8. The recombinant fusion protein of respiratory syncytial virus according to claim 3, wherein the recombinant fusion protein of respiratory syncytial virus has the N-terminus of the bacteriophage T4 fibritin foldon domain polypeptide having SEQ ID NO: 23 linked to the C-terminus of the fusion protein (F protein) by a KLSG (SEQ ID NO: 99) linker, and has the N-terminus of the recombinant D1 domain polypeptide of the flagellin protein having SEQ ID NO: 24 linked to the C-terminus of the bacteriophage T4 fibritin foldon domain polypeptide having SEQ ID NO: 23 by a GGGS (SEQ ID NO: 100) linker.

9. The recombinant fusion protein of respiratory syncytial virus according to claim 8, wherein the recombinant fusion protein of respiratory syncytial virus has an amino acid sequence selected from SEQ ID NOS: 49-69.

10. A recombinant fusion protein (F protein) of respiratory syncytial virus (RSV), wherein:
a recombinant D1 domain polypeptide of the flagellin protein having SEQ ID NO: 24 is linked at the C-terminus of a fusion protein (F protein) with the transmembrane domain of the wild-type respiratory syncytial virus (RSV) fusion protein (F protein) deleted; and
the fusion protein (F protein) with the transmembrane domain of the wild-type respiratory syncytial virus (RSV) fusion protein (F protein) deleted has an amino acid sequence selected from SEQ ID NOS: 3-22.

11. The recombinant fusion protein of respiratory syncytial virus according to claim 10, wherein the N-terminus of the recombinant D1 domain polypeptide of the flagellin protein having SEQ ID NO: 24 is linked to the C-terminus of the fusion protein (F protein), and the fusion protein (F protein) and the recombinant D1 domain polypeptide of the flagellin protein are covalently bonded by a KLGGGS (SEQ ID NO: 101) linker.

12. The recombinant fusion protein of respiratory syncytial virus according to claim 11, wherein the recombinant fusion protein of respiratory syncytial virus has an amino acid sequence selected from SEQ ID NOS: 70-90.

13. A nucleic acid encoding the recombinant fusion protein of respiratory syncytial virus according to claim 1.

14. An isolated cell or a virus comprising the nucleic acid according to claim 13.

15. An immunogenic composition capable of inducing an immune response in a host, comprising the recombinant fusion protein of respiratory syncytial virus according to claim 1 and a pharmaceutically acceptable carrier.

16. A medicine for treating or inhibiting respiratory syncytial viral infection, comprising the recombinant fusion protein according to claim 1 as an antigen.

* * * * *

SEQUENCE LISTING

```
<160> NUMBER OF SEQ ID NOS: 104

<210> SEQ ID NO 1
<211> LENGTH: 574
<212> TYPE: PRT
<213> ORGANISM: respiratory syncytial virus

<400> SEQUENCE: 1

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255
```

| | | | | | | | | | | | |
|---|---|---|---|---|---|---|---|---|---|---|---|
|Leu|Leu|Ser|Leu|Ile|Asn|Asp|Met|Pro|Ile|Thr|Asn|Asp|Gln|Lys|Lys|
| | |   |260|   |   |   |   |265|   |   |   |   |270|   |   |

Leu Leu Ser Leu Ile Asn Asp Met Pro Ile Thr Asn Asp Gln Lys Lys
              260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
    515                 520                 525

Ala Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 2
<211> LENGTH: 524
<212> TYPE: PRT
<213> ORGANISM: respiratory syncytial virus

<400> SEQUENCE: 2

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

```
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Ser Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480
```

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520
```

<210> SEQ ID NO 3
<211> LENGTH: 524
<212> TYPE: PRT
<213> ORGANISM: Artificial Sequence
<220> FEATURE:
<223> OTHER INFORMATION: SK-FP1 aa

<400> SEQUENCE: 3

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Arg Ala Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Ala Ala Gly Ala Ala Ala Gly Ala
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320
```

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn
                515                 520

<210> SEQ ID NO 4
<211> LENGTH: 524
<212> TYPE: PRT
<213> ORGANISM: Artificial Sequence
<220> FEATURE:
<223> OTHER INFORMATION: SK-FP3 aa

<400> SEQUENCE: 4

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Gln Asn Gly Gln Asn Asn Gly Ser
    130                 135                 140

Gly Ser Ala Ile Ala Ser Gly Ile Ala Val Ser Lys Val Leu His Leu
145                 150                 155                 160
```

```
Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 5
<211> LENGTH: 524
<212> TYPE: PRT
<213> ORGANISM: Artificial Sequence
<220> FEATURE:
<223> OTHER INFORMATION: SK-FP4 aa

<400> SEQUENCE: 5
```

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Asn Ser Gly Asn Ser Ser Gly Gly
            130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
```

```
                420             425             430
Lys Thr Phe Ser Asn Gly Cys Asp Tyr Val Ser Asn Lys Gly Val Asp
            435             440             445
Thr Val Ser Val Gly Asn Thr Leu Tyr Tyr Val Asn Lys Leu Glu Gly
            450             455             460
Lys Asn Leu Tyr Val Lys Gly Glu Pro Ile Ile Asn Tyr Tyr Asp Pro
465             470             475             480
Leu Val Phe Pro Ser Asp Glu Phe Asp Ala Ser Ile Ser Gln Val Asn
            485             490             495
Glu Lys Ile Asn Gln Ser Leu Ala Phe Ile Arg Arg Ser Asp Glu Leu
            500             505             510
Leu His Asn Val Asn Thr Gly Lys Ser Thr Thr Asn
            515             520

<210> SEQ ID NO 6
<211> LENGTH: 524
<212> TYPE: PRT
<213> ORGANISM: Artificial Sequence
<220> FEATURE:
<223> OTHER INFORMATION: SK-FP6 aa

<400> SEQUENCE: 6

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
                20                  25                  30
Tyr Gln Ser Thr Cys Ser Ala Val Ser Arg Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
        115                 120                 125
Ile Ser Lys Lys Arg Lys Arg Arg Thr Leu Ser Lys Lys Arg Lys Arg
        130                 135                 140
Arg Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
    210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
```

-continued

```
                260                 265                 270
Leu Met Ser Ser Asn Val Gln Ile Val Arg Gln Gln Ser Tyr Ser Ile
            275                 280                 285
Met Ser Ile Ile Lys Glu Glu Val Leu Ala Tyr Val Gln Leu Pro
        290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn
        515                 520

<210> SEQ ID NO 7
<211> LENGTH: 524
<212> TYPE: PRT
<213> ORGANISM: Artificial Sequence
<220> FEATURE:
<223> OTHER INFORMATION: SK-Seq 1_dTM_F140W

<400> SEQUENCE: 7

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val Ser Arg Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
```

-continued

```
                100                 105                 110
Gln Tyr Met Asn Tyr Thr Ile Asn Thr Thr Lys Asn Leu Asn Val Ser
            115                 120                 125
Ile Ser Lys Lys Arg Lys Arg Arg Phe Leu Gly Trp Leu Leu Gly Val
        130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
            210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
        290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
            355                 360                 365
Thr Met Asn Ser Leu Thr Leu Pro Ser Glu Val Ser Leu Cys Asn Thr
        370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Leu Glu Gly
            450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn
        515                 520
```

<210> SEQ ID NO 8
<211> LENGTH: 524
<212> TYPE: PRT
<213> ORGANISM: Artificial Sequence
<220> FEATURE:
<223> OTHER INFORMATION: SK-Seq 1_dTM_E163Q

<400> SEQUENCE: 8

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365
```

```
Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
            515                 520

<210> SEQ ID NO 9
<211> LENGTH: 524
<212> TYPE: PRT
<213> ORGANISM: Artificial Sequence
<220> FEATURE:
<223> OTHER INFORMATION: SK-Seq 1_dTM_V179L

<400> SEQUENCE: 9

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
            130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Leu Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205
```

-continued

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 10
<211> LENGTH: 524
<212> TYPE: PRT
<213> ORGANISM: Artificial Sequence
<220> FEATURE:
<223> OTHER INFORMATION: SK-Seq 1_dTM_L188Q

<400> SEQUENCE: 10

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

```
Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Gln Thr Ser Lys Val
            180                 185                 190

Leu Asp Leu Lys Asn Tyr Ile Asn Asn Gln Leu Leu Pro Ile Val Asn
    195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
    450                 455                 460
```

-continued

```
Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn
        515                 520
```

<210> SEQ ID NO 11
<211> LENGTH: 524
<212> TYPE: PRT
<213> ORGANISM: Artificial Sequence
<220> FEATURE:
<223> OTHER INFORMATION: SK-Seq 1_dTM_T189L

<400> SEQUENCE: 11

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300
```

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
            515                 520

<210> SEQ ID NO 12
<211> LENGTH: 524
<212> TYPE: PRT
<213> ORGANISM: Artificial Sequence
<220> FEATURE:
<223> OTHER INFORMATION: SK-Seq 1_dTM_E487L

<400> SEQUENCE: 12

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

```
Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 13
<211> LENGTH: 524
<212> TYPE: PRT
<213> ORGANISM: Artificial Sequence
<220> FEATURE:
<223> OTHER INFORMATION: SK-Seq 1_dTM_F505W
```

<400> SEQUENCE: 13

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
```

-continued

```
                    405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Leu Glu Gly
        450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Trp Ile Arg Arg Ser Asp Glu Leu
                500                 505                 510
Leu His Asn Val Asn Thr Gly Lys Ser Thr Thr Asn
            515                 520

<210> SEQ ID NO 14
<211> LENGTH: 524
<212> TYPE: PRT
<213> ORGANISM: Artificial Sequence
<220> FEATURE:
<223> OTHER INFORMATION: SK-Seq 1_dTM_F140W_E163Q

<400> SEQUENCE: 14

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val Ser Arg Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
        115                 120                 125
Ile Ser Lys Lys Arg Lys Arg Arg Phe Leu Gly Trp Leu Leu Gly Val
    130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
    210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
```

-continued

```
                    245                 250                 255
Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 15
<211> LENGTH: 524
<212> TYPE: PRT
<213> ORGANISM: Artificial Sequence
<220> FEATURE:
<223> OTHER INFORMATION: SK-Seq 1_dTM_F140W_E163Q_L188Q_T189L

<400> SEQUENCE: 15

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
```

-continued

Met Gln Asn Thr Pro Ala Ala Asn Asn Arg Ala Arg Arg Glu Ala Pro
                85                  90                  95
                              100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Trp Leu Leu Gly Val
        130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn
        515                 520

<210> SEQ ID NO 16
<211> LENGTH: 524
<212> TYPE: PRT
<213> ORGANISM: Artificial Sequence
<220> FEATURE:
<223> OTHER INFORMATION: SK-Seq 1_dTM_F488W_E163Q

<400> SEQUENCE: 16

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

```
Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
        405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn
        515                 520

<210> SEQ ID NO 17
<211> LENGTH: 524
<212> TYPE: PRT
<213> ORGANISM: Artificial Sequence
<220> FEATURE:
<223> OTHER INFORMATION: SK-Seq 1_dTM_F488W_V179L

<400> SEQUENCE: 17

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65              70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
            180                 185                 190
```

```
Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn
    515                 520

<210> SEQ ID NO 18
<211> LENGTH: 524
<212> TYPE: PRT
<213> ORGANISM: Artificial Sequence
<220> FEATURE:
<223> OTHER INFORMATION: SK-Seq 1_dTM_F505W_F140W

<400> SEQUENCE: 18

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30
```

```
            Tyr Gln Ser Thr Cys Ser Ala Val Ser Arg Gly Tyr Leu Ser Ala Leu
                    35                  40                  45

Arg Thr Gly Trp Tyr Thr Ser Val Ile Thr Ile Glu Leu Ser Asn Ile
            50                  55                  60

Lys Glu Thr Lys Cys Asn Gly Thr Asp Thr Lys Val Lys Leu Ile Lys
            65                  70                  75                  80

Gln Glu Leu Asp Lys Tyr Lys Asn Ala Val Thr Glu Leu Gln Leu Leu
                                85                  90                  95

Met Gln Asn Thr Pro Ala Ala Asn Asn Arg Ala Arg Arg Glu Ala Pro
                        100                 105                 110

Gln Tyr Met Asn Tyr Thr Ile Asn Thr Thr Lys Asn Leu Asn Val Ser
                        115                 120                 125

Ile Ser Lys Lys Arg Lys Arg Arg Phe Leu Gly Trp Leu Leu Gly Val
                        130                 135                 140

Gly Ser Ala Ile Ala Ser Gly Ile Ala Val Ser Lys Val Leu His Leu
            145                 150                 155                 160

Glu Gly Glu Val Asn Lys Ile Lys Asn Ala Leu Leu Ser Thr Asn Lys
                                165                 170                 175

Ala Val Val Ser Leu Ser Asn Gly Val Ser Val Leu Thr Ser Lys Val
                        180                 185                 190

Leu Asp Leu Lys Asn Tyr Ile Asn Asn Gln Leu Leu Pro Ile Val Asn
                        195                 200                 205

Gln Gln Ser Cys Arg Ile Ser Asn Ile Glu Thr Val Ile Glu Phe Gln
                        210                 215                 220

Gln Lys Asn Ser Arg Leu Leu Glu Ile Thr Arg Glu Phe Ser Val Asn
            225                 230                 235                 240

Ala Gly Val Thr Thr Pro Leu Ser Thr Tyr Met Leu Thr Asn Ser Glu
                        245                 250                 255

Leu Leu Ser Leu Ile Asn Asp Met Pro Ile Thr Asn Asp Gln Lys Lys
                        260                 265                 270

Leu Met Ser Ser Asn Val Gln Ile Val Arg Gln Gln Ser Tyr Ser Ile
                        275                 280                 285

Met Ser Ile Ile Lys Glu Glu Val Leu Ala Tyr Val Val Gln Leu Pro
                        290                 295                 300

Ile Tyr Gly Val Ile Asp Thr Pro Cys Trp Lys Leu His Thr Ser Pro
            305                 310                 315                 320

Leu Cys Thr Thr Asn Ile Lys Glu Gly Ser Asn Ile Cys Leu Thr Arg
                        325                 330                 335

Thr Asp Arg Gly Trp Tyr Cys Asp Asn Ala Gly Ser Val Ser Phe Phe
                        340                 345                 350

Pro Gln Ala Asp Thr Cys Lys Val Gln Ser Asn Arg Val Phe Cys Asp
                        355                 360                 365

Thr Met Asn Ser Leu Thr Leu Pro Ser Glu Val Ser Leu Cys Asn Thr
                        370                 375                 380

Asp Ile Phe Asn Ser Lys Tyr Asp Cys Lys Ile Met Thr Ser Lys Thr
            385                 390                 395                 400

Asp Ile Ser Ser Ser Val Ile Thr Ser Leu Gly Ala Ile Val Ser Cys
                        405                 410                 415

Tyr Gly Lys Thr Lys Cys Thr Ala Ser Asn Lys Asn Arg Gly Ile Ile
                        420                 425                 430

Lys Thr Phe Ser Asn Gly Cys Asp Tyr Val Ser Asn Lys Gly Val Asp
                        435                 440                 445
```

```
Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn
            515                 520
```

<210> SEQ ID NO 19
<211> LENGTH: 524
<212> TYPE: PRT
<213> ORGANISM: Artificial Sequence
<220> FEATURE:
<223> OTHER INFORMATION: SK-Seq 1_dTM_E487L_F505W

<400> SEQUENCE: 19

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn
        515                 520

<210> SEQ ID NO 20
<211> LENGTH: 524
<212> TYPE: PRT
<213> ORGANISM: Artificial Sequence
<220> FEATURE:
<223> OTHER INFORMATION: SK-Seq 1_dTM_ F505W_E163Q

<400> SEQUENCE: 20

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125
```

```
Ile Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Val Asn Lys Leu Glu Gly
450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Trp Ile Arg Arg Ser Asp Glu Leu
            500                 505                 510
Leu His Asn Val Asn Thr Gly Lys Ser Thr Thr Asn
        515                 520

<210> SEQ ID NO 21
<211> LENGTH: 524
<212> TYPE: PRT
```

<213> ORGANISM: Artificial Sequence
<220> FEATURE:
<223> OTHER INFORMATION: SK-Seq 1_dTM_L188Q_T189L_ F505W

<400> SEQUENCE: 21

| Met | Glu | Leu | Leu | Ile | His | Arg | Ser | Ser | Ala | Ile | Phe | Leu | Thr | Leu | Ala |
|-----|-----|-----|-----|-----|-----|-----|-----|-----|-----|-----|-----|-----|-----|-----|-----|
| 1 | | | | 5 | | | | | 10 | | | | | 15 | |

| Ile | Asn | Ala | Phe | Tyr | Leu | Thr | Ser | Ser | Gln | Asn | Ile | Thr | Glu | Glu | Phe |
| | | | 20 | | | | | 25 | | | | | 30 | | |

| Tyr | Gln | Ser | Thr | Cys | Ser | Ala | Val | Ser | Arg | Gly | Tyr | Leu | Ser | Ala | Leu |
| | | 35 | | | | | 40 | | | | | 45 | | | |

| Arg | Thr | Gly | Trp | Tyr | Thr | Ser | Val | Ile | Thr | Ile | Glu | Leu | Ser | Asn | Ile |
| 50 | | | | | 55 | | | | | 60 | | | | | |

| Lys | Glu | Thr | Lys | Cys | Asn | Gly | Thr | Asp | Thr | Lys | Val | Lys | Leu | Ile | Lys |
| 65 | | | | | 70 | | | | | 75 | | | | | 80 |

| Gln | Glu | Leu | Asp | Lys | Tyr | Lys | Asn | Ala | Val | Thr | Glu | Leu | Gln | Leu | Leu |
| | | | | 85 | | | | | 90 | | | | | 95 | |

| Met | Gln | Asn | Thr | Pro | Ala | Ala | Asn | Asn | Arg | Ala | Arg | Arg | Glu | Ala | Pro |
| | | | 100 | | | | | 105 | | | | | 110 | | |

| Gln | Tyr | Met | Asn | Tyr | Thr | Ile | Asn | Thr | Thr | Lys | Asn | Leu | Asn | Val | Ser |
| | | 115 | | | | | 120 | | | | | 125 | | | |

| Ile | Ser | Lys | Lys | Arg | Lys | Arg | Arg | Phe | Leu | Gly | Phe | Leu | Leu | Gly | Val |
| | 130 | | | | | 135 | | | | | 140 | | | | |

| Gly | Ser | Ala | Ile | Ala | Ser | Gly | Ile | Ala | Val | Ser | Lys | Val | Leu | His | Leu |
| 145 | | | | | 150 | | | | | 155 | | | | | 160 |

| Glu | Gly | Glu | Val | Asn | Lys | Ile | Lys | Asn | Ala | Leu | Leu | Ser | Thr | Asn | Lys |
| | | | | 165 | | | | | 170 | | | | | 175 | |

| Ala | Val | Val | Ser | Leu | Ser | Asn | Gly | Val | Ser | Val | Gln | Leu | Ser | Lys | Val |
| | | | 180 | | | | | 185 | | | | | 190 | | |

| Leu | Asp | Leu | Lys | Asn | Tyr | Ile | Asn | Asn | Gln | Leu | Leu | Pro | Ile | Val | Asn |
| | | 195 | | | | | 200 | | | | | 205 | | | |

| Gln | Gln | Ser | Cys | Arg | Ile | Ser | Asn | Ile | Glu | Thr | Val | Ile | Glu | Phe | Gln |
| | 210 | | | | | 215 | | | | | 220 | | | | |

| Gln | Lys | Asn | Ser | Arg | Leu | Leu | Glu | Ile | Thr | Arg | Glu | Phe | Ser | Val | Asn |
| 225 | | | | | 230 | | | | | 235 | | | | | 240 |

| Ala | Gly | Val | Thr | Thr | Pro | Leu | Ser | Thr | Tyr | Met | Leu | Thr | Asn | Ser | Glu |
| | | | | 245 | | | | | 250 | | | | | 255 | |

| Leu | Leu | Ser | Leu | Ile | Asn | Asp | Met | Pro | Ile | Thr | Asn | Asp | Gln | Lys | Lys |
| | | | 260 | | | | | 265 | | | | | 270 | | |

| Leu | Met | Ser | Ser | Asn | Val | Gln | Ile | Val | Arg | Gln | Gln | Ser | Tyr | Ser | Ile |
| | | 275 | | | | | 280 | | | | | 285 | | | |

| Met | Ser | Ile | Ile | Lys | Glu | Glu | Val | Leu | Ala | Tyr | Val | Val | Gln | Leu | Pro |
| | 290 | | | | | 295 | | | | | 300 | | | | |

| Ile | Tyr | Gly | Val | Ile | Asp | Thr | Pro | Cys | Trp | Lys | Leu | His | Thr | Ser | Pro |
| 305 | | | | | 310 | | | | | 315 | | | | | 320 |

| Leu | Cys | Thr | Thr | Asn | Ile | Lys | Glu | Gly | Ser | Asn | Ile | Cys | Leu | Thr | Arg |
| | | | | 325 | | | | | 330 | | | | | 335 | |

| Thr | Asp | Arg | Gly | Trp | Tyr | Cys | Asp | Asn | Ala | Gly | Ser | Val | Ser | Phe | Phe |
| | | | 340 | | | | | 345 | | | | | 350 | | |

| Pro | Gln | Ala | Asp | Thr | Cys | Lys | Val | Gln | Ser | Asn | Arg | Val | Phe | Cys | Asp |
| | | 355 | | | | | 360 | | | | | 365 | | | |

| Thr | Met | Asn | Ser | Leu | Thr | Leu | Pro | Ser | Glu | Val | Ser | Leu | Cys | Asn | Thr |
| | 370 | | | | | 375 | | | | | 380 | | | | |

| Asp | Ile | Phe | Asn | Ser | Lys | Tyr | Asp | Cys | Lys | Ile | Met | Thr | Ser | Lys | Thr |

```
385                 390                 395                 400
Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
                450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
                500                 505                 510

Leu His Asn Val Asn Thr Gly Lys Ser Thr Thr Asn
                515                 520

<210> SEQ ID NO 22
<211> LENGTH: 524
<212> TYPE: PRT
<213> ORGANISM: Artificial Sequence
<220> FEATURE:
<223> OTHER INFORMATION: SK-Seq 1_dTM_E487L_E163Q

<400> SEQUENCE: 22

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
                35                  40                  45

Arg Thr Gly Trp Tyr Thr Ser Val Ile Thr Ile Glu Leu Ser Asn Ile
            50                  55                  60

Lys Glu Thr Lys Cys Asn Gly Thr Asp Thr Lys Val Lys Leu Ile Lys
65              70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
                115                 120                 125

Ile Ser Lys Lys Arg Lys Arg Arg Phe Leu Gly Phe Leu Leu Gly Val
                130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
                195                 200                 205

Gln Gln Ser Cys Arg Ile Ser Asn Ile Glu Thr Val Ile Glu Phe Gln
                210                 215                 220

Gln Lys Asn Ser Arg Leu Leu Glu Ile Thr Arg Glu Phe Ser Val Asn
```

-continued

```
                225                 230                 235                 240
Ala Gly Val Thr Thr Pro Leu Ser Thr Tyr Met Leu Thr Asn Ser Glu
                    245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                    485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn
            515                 520

<210> SEQ ID NO 23
<211> LENGTH: 27
<212> TYPE: PRT
<213> ORGANISM: Unknown
<220> FEATURE:
<223> OTHER INFORMATION: foldon domain of phage T4 fibritin

<400> SEQUENCE: 23

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 24
<211> LENGTH: 166
<212> TYPE: PRT
<213> ORGANISM: Artificial Sequence
<220> FEATURE:
<223> OTHER INFORMATION: SK_fla
```

```
<400> SEQUENCE: 24

Thr Ser Asn Ile Lys Gly Leu Thr Gln Ala Ser Arg Asn Ala Asn Asp
1               5                   10                  15

Gly Ile Ser Ile Ala Gln Thr Thr Glu Gly Ala Leu Asn Glu Ile Asn
                20                  25                  30

Asn Asn Leu Gln Arg Val Arg Glu Leu Ser Val Gln Ala Thr Asn Gly
            35                  40                  45

Thr Asn Ser Asp Ser Asp Leu Lys Ser Ile Gln Asp Glu Ile Gln Gln
    50                  55                  60

Arg Leu Glu Glu Ile Asp Arg Val Ser Asn Gln Thr Gln Phe Asn Gly
65                  70                  75                  80

Val Lys Val Leu Ser Gln Asp Asn Gln Met Lys Ile Gln Val Gly Ala
                85                  90                  95

Asn Asp Gly Glu Thr Ile Thr Ile Asp Leu Gln Lys Ile Asp Val Lys
            100                 105                 110

Ser Leu Gly Leu Asp Gly Phe Asn Val Asn Gly Gly Ser Thr Ala Asn
            115                 120                 125

Pro Leu Ala Ser Ile Asp Ser Ala Leu Ser Lys Val Asp Ala Val Arg
    130                 135                 140

Ser Ser Leu Gly Ala Ile Gln Asn Arg Phe Asp Ser Ala Ile Thr Asn
145                 150                 155                 160

Leu Gly Asn Thr Val Thr
                165

<210> SEQ ID NO 25
<211> LENGTH: 31
<212> TYPE: PRT
<213> ORGANISM: Artificial Sequence
<220> FEATURE:
<223> OTHER INFORMATION: KLSG-foldon

<400> SEQUENCE: 25

Lys Leu Ser Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu
                20                  25                  30

<210> SEQ ID NO 26
<211> LENGTH: 201
<212> TYPE: PRT
<213> ORGANISM: Artificial Sequence
<220> FEATURE:
<223> OTHER INFORMATION: KLSG-foldon-GGGS-flagellin D1

<400> SEQUENCE: 26

Lys Leu Ser Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu Gly
                20                  25                  30

Gly Gly Ser Thr Ser Asn Ile Lys Gly Leu Thr Gln Ala Ser Arg Asn
            35                  40                  45

Ala Asn Asp Gly Ile Ser Ile Ala Gln Thr Thr Glu Gly Ala Leu Asn
    50                  55                  60

Glu Ile Asn Asn Asn Leu Gln Arg Val Arg Glu Leu Ser Val Gln Ala
65                  70                  75                  80

Thr Asn Gly Thr Asn Ser Asp Ser Asp Leu Lys Ser Ile Gln Asp Glu
                85                  90                  95
```

```
Ile Gln Gln Arg Leu Glu Ile Asp Arg Val Ser Asn Gln Thr Gln
            100                 105                 110

Phe Asn Gly Val Lys Val Leu Ser Gln Asp Asn Gln Met Lys Ile Gln
            115                 120                 125

Val Gly Ala Asn Asp Gly Glu Thr Ile Thr Ile Asp Leu Gln Lys Ile
130                 135                 140

Asp Val Lys Ser Leu Gly Leu Asp Gly Phe Asn Val Asn Gly Ser
145                 150                 155                 160

Thr Ala Asn Pro Leu Ala Ser Ile Asp Ser Ala Leu Ser Lys Val Asp
                165                 170                 175

Ala Val Arg Ser Ser Leu Gly Ala Ile Gln Asn Arg Phe Asp Ser Ala
            180                 185                 190

Ile Thr Asn Leu Gly Asn Thr Val Thr
            195                 200

<210> SEQ ID NO 27
<211> LENGTH: 172
<212> TYPE: PRT
<213> ORGANISM: Artificial Sequence
<220> FEATURE:
<223> OTHER INFORMATION: KLGGGS + flagellin D1

<400> SEQUENCE: 27

Lys Leu Gly Gly Gly Ser Thr Ser Asn Ile Lys Gly Leu Thr Gln Ala
1               5                   10                  15

Ser Arg Asn Ala Asn Asp Gly Ile Ser Ile Ala Gln Thr Thr Glu Gly
            20                  25                  30

Ala Leu Asn Glu Ile Asn Asn Asn Leu Gln Arg Val Arg Glu Leu Ser
        35                  40                  45

Val Gln Ala Thr Asn Gly Thr Asn Ser Asp Ser Asp Leu Lys Ser Ile
    50                  55                  60

Gln Asp Glu Ile Gln Gln Arg Leu Glu Ile Asp Arg Val Ser Asn
65                  70                  75                  80

Gln Thr Gln Phe Asn Gly Val Lys Val Leu Ser Gln Asp Asn Gln Met
                85                  90                  95

Lys Ile Gln Val Gly Ala Asn Asp Gly Glu Thr Ile Thr Ile Asp Leu
            100                 105                 110

Gln Lys Ile Asp Val Lys Ser Leu Gly Leu Asp Gly Phe Asn Val Asn
        115                 120                 125

Gly Gly Ser Thr Ala Asn Pro Leu Ala Ser Ile Asp Ser Ala Leu Ser
    130                 135                 140

Lys Val Asp Ala Val Arg Ser Ser Leu Gly Ala Ile Gln Asn Arg Phe
145                 150                 155                 160

Asp Ser Ala Ile Thr Asn Leu Gly Asn Thr Val Thr
                165                 170

<210> SEQ ID NO 28
<211> LENGTH: 555
<212> TYPE: PRT
<213> ORGANISM: Artificial Sequence
<220> FEATURE:
<223> OTHER INFORMATION: RFP-RSV_1

<400> SEQUENCE: 28

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
```

-continued

```
                20                  25                  30
Tyr Gln Ser Thr Cys Ser Ala Val Ser Arg Gly Tyr Leu Ser Ala Leu
                35                  40                  45
Arg Thr Gly Trp Tyr Thr Ser Val Ile Thr Ile Glu Leu Ser Asn Ile
            50                  55                  60
Lys Glu Thr Lys Cys Asn Gly Thr Asp Thr Lys Val Lys Leu Ile Lys
 65                  70                  75                  80
Gln Glu Leu Asp Lys Tyr Lys Asn Ala Val Thr Glu Leu Gln Leu Leu
                    85                  90                  95
Met Gln Asn Thr Pro Ala Ala Asn Asn Arg Ala Arg Arg Glu Ala Pro
                100                 105                 110
Gln Tyr Met Asn Tyr Thr Ile Asn Thr Thr Lys Asn Leu Asn Val Ser
                115                 120                 125
Ile Ser Lys Lys Arg Lys Arg Arg Phe Leu Gly Phe Leu Leu Gly Val
                130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                    165                 170                 175
Ala Val Val Ser Leu Ser Asn Gly Val Ser Val Leu Thr Ser Lys Val
                180                 185                 190
Leu Asp Leu Lys Asn Tyr Ile Asn Asn Gln Leu Leu Pro Ile Val Asn
                195                 200                 205
Gln Gln Ser Cys Arg Ile Ser Asn Ile Glu Thr Val Ile Glu Phe Gln
                210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                    245                 250                 255
Leu Leu Ser Leu Ile Asn Asp Met Pro Ile Thr Asn Asp Gln Lys Lys
                260                 265                 270
Leu Met Ser Ser Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
                290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                    325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
                355                 360                 365
Thr Met Asn Ser Leu Thr Leu Pro Ser Glu Val Ser Leu Cys Asn Thr
                370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                    405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
```

Thr Val Ser Val Gly Asn Thr Leu Tyr Tyr Val Asn Lys Leu Glu Gly
              450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555

<210> SEQ ID NO 29
<211> LENGTH: 555
<212> TYPE: PRT
<213> ORGANISM: Artificial Sequence
<220> FEATURE:
<223> OTHER INFORMATION: RFP-RSV_2

<400> SEQUENCE: 29

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Ala Ala Gly Ala Ala Ala Gly Ala
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
530                 535                 540

Asp Gly Glu Trp Val Leu Leu Ser Thr Phe Leu
545                 550                 555

<210> SEQ ID NO 30
<211> LENGTH: 555
<212> TYPE: PRT
<213> ORGANISM: Artificial Sequence
<220> FEATURE:
<223> OTHER INFORMATION: RFP-RSV_3

<400> SEQUENCE: 30

Met Glu Leu Leu Ile His Arg Ser Ser Ala Ile Phe Le

```
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Gln Asn Gly Gln Asn Asn Gly Ser
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480
```

-continued

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 31
<211> LENGTH: 555
<212> TYPE: PRT
<213> ORGANISM: Artificial Sequence
<220> FEATURE:
<223> OTHER INFORMATION: RFP-RSV_4

<400> SEQUENCE: 31

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Asn Ser Gly Asn Ser Ser Gly Gly
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
    290                 295                 300

```
Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Thr Leu Ser Lys Lys Arg Lys Arg
130                 135                 140

Arg Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
```

```
            515                 520                 525
Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555

<210> SEQ ID NO 33
<211> LENGTH: 555
<212> TYPE: PRT
<213> ORGANISM: Artificial Sequence
<220> FEATURE:
<223> OTHER INFORMATION: RFP-RSV_6

<400> SEQUENCE: 33

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
```

```
              325                 330                 335
Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555
```

<210> SEQ ID NO 34
<211> LENGTH: 555
<212> TYPE: PRT
<213> ORGANISM: Artificial Sequence
<220> FEATURE:
<223> OTHER INFORMATION: RFP-RSV_7

<400> SEQUENCE: 34

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
```

```
            130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asn Asn Gln Leu Leu Pro Ile Val Asn
            195                 200                 205
Gln Gln Ser Cys Arg Ile Ser Asn Ile Glu Thr Val Ile Glu Phe Gln
210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
            355                 360                 365
Thr Met Asn Ser Leu Thr Leu Pro Ser Glu Val Ser Leu Cys Asn Thr
370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Leu Glu Gly
            450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Lys Leu Ser Gly
            515                 520                 525
Gly Tyr Ile Pro Glu Ala Pro Arg Asp Gly Gln Ala Tyr Val Arg Lys
            530                 535                 540
Asp Gly Glu Trp Val Leu Leu Ser Thr Phe Leu
545                 550                 555
```

<210> SEQ ID NO 35
<211> LENGTH: 555
<212> TYPE: PRT
<213> ORGANISM: Artificial Sequence
<220> FEATURE:
<223> OTHER INFORMATION: RFP-RSV_8

<400> SEQUENCE: 35

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365
```

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555

<210> SEQ ID NO 36
<211> LENGTH: 555
<212> TYPE: PRT
<213> ORGANISM: Artificial Sequence
<220> FEATURE:
<223> OTHER INFORMATION: RFP-RSV_9

<400> SEQUENCE: 36

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

```
Ala Val Val Ser Leu Ser Asn Gly Val Ser Gln Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
530                 535                 540

Asp Gly Glu Trp Val Leu Leu Ser Thr Phe Leu
545                 550                 555

<210> SEQ ID NO 37
<211> LENGTH: 555
<212> TYPE: PRT
<213> ORGANISM: Artificial Sequence
<220> FEATURE:
```

<223> OTHER INFORMATION: RFP-RSV_10

<400> SEQUENCE: 37

```
Met Glu Leu Leu Ile His Arg Ser Ser Ala Ile Phe Le

-continued

```
Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 38
<211> LENGTH: 555
<212> TYPE: PRT
<213> ORGANISM: Artificial Sequence
<220> FEATURE:
<223> OTHER INFORMATION: RFP-RSV_11

<400> SEQUENCE: 38

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205
```

```
Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 39
<211> LENGTH: 555
<212> TYPE: PRT
<213> ORGANISM: Artificial Sequence
<220> FEATURE:
<223> OTHER INFORMATION: RFP-RSV_12

<400> SEQUENCE: 39

Met Glu Leu Leu Ile His Arg Ser Ser Ala Ile Phe Leu Thr Leu Ala
1               5                   10                  15
```

-continued

Ile Asn Ala Phe Tyr Leu Thr Ser Ser Gln Asn Ile Thr Glu Phe
              20                  25                  30

Tyr Gln Ser Thr Cys Ser Ala Val Ser Arg Gly Tyr Leu Ser Ala Leu
         35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Arg Glu Ala Pro
             100                 105                 110

Gln Tyr Met Asn Tyr Thr Ile Asn Thr Thr Lys Asn Leu Asn Val Ser
         115                 120                 125

Ile Ser Lys Lys Arg Lys Arg Arg Phe Leu Gly Phe Leu Leu Gly Val
         130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                 165                 170                 175

Ala Val Val Ser Leu Ser Asn Gly Val Ser Val Leu Thr Ser Lys Val
             180                 185                 190

Leu Asp Leu Lys Asn Tyr Ile Asn Asn Gln Leu Leu Pro Ile Val Asn
         195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
             245                 250                 255

Leu Leu Ser Leu Ile Asn Asp Met Pro Ile Thr Asn Asp Gln Lys Lys
         260                 265                 270

Leu Met Ser Ser Asn Val Gln Ile Val Arg Gln Gln Ser Tyr Ser Ile
         275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
             325                 330                 335

Thr Asp Arg Gly Trp Tyr Cys Asp Asn Ala Gly Ser Val Ser Phe Phe
         340                 345                 350

Pro Gln Ala Asp Thr Cys Lys Val Gln Ser Asn Arg Val Phe Cys Asp
         355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
             405                 410                 415

Tyr Gly Lys Thr Lys Cys Thr Ala Ser Asn Lys Asn Arg Gly Ile Ile
         420                 425                 430

Lys Thr Phe Ser Asn Gly Cys Asp Tyr Val Ser Asn Lys Gly Val Asp

```
                435                 440                 445
Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
            530                 535                 540

Asp Gly Glu Trp Val Leu Leu Ser Thr Phe Leu
545                 550                 555

<210> SEQ ID NO 40
<211> LENGTH: 555
<212> TYPE: PRT
<213> ORGANISM: Artificial Sequence
<220> FEATURE:
<223> OTHER INFORMATION: RFP-RSV_13

<400> SEQUENCE: 40

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
```

-continued

```
                    245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Lys Leu Ser Gly
        515                 520                 525
Gly Tyr Ile Pro Glu Ala Pro Arg Asp Gly Gln Ala Tyr Val Arg Lys
    530                 535                 540
Asp Gly Glu Trp Val Leu Leu Ser Thr Phe Leu
545                 550                 555
```

<210> SEQ ID NO 41
<211> LENGTH: 555
<212> TYPE: PRT
<213> ORGANISM: Artificial Sequence
<220> FEATURE:
<223> OTHER INFORMATION: RFP-RSV_14

<400> SEQUENCE: 41

```
Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val Ser Arg Gly Tyr Leu Ser Ala Leu
        35                  40                  45
Arg Thr Gly Trp Tyr Thr Ser Val Ile Thr Ile Glu Leu Ser Asn Ile
```

```
                50                  55                  60
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Trp Leu Leu Gly Val
        130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480
```

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 42
<211> LENGTH: 555
<212> TYPE: PRT
<213> ORGANISM: Artificial Sequence
<220> FEATURE:
<223> OTHER INFORMATION: RFP-RSV_15

<400> SEQUENCE: 42

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285
```

```
Met Ser Ile Ile Lys Glu Glu Val Leu Ala Tyr Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
                355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
                515                 520                 525

Gly Tyr Ile Pro Glu Ala Pro Arg Asp Gly Gln Ala Tyr Val Arg Lys
                530                 535                 540

Asp Gly Glu Trp Val Leu Leu Ser Thr Phe Leu
545                 550                 555

<210> SEQ ID NO 43
<211> LENGTH: 555
<212> TYPE: PRT
<213> ORGANISM: Artificial Sequence
<220> FEATURE:
<223> OTHER INFORMATION: RFP-RSV_16

<400> SEQUENCE: 43

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
                35                  40                  45

Arg Thr Gly Trp Tyr Thr Ser Val Ile Thr Ile Glu Leu Ser Asn Ile
            50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Asn Thr Pro Ala Ala Asn Asn Arg Ala Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510
```

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555

<210> SEQ ID NO 44
<211> LENGTH: 555
<212> TYPE: PRT
<213> ORGANISM: Artificial Sequence
<220> FEATURE:
<223> OTHER INFORMATION: RFP-RSV_17

<400> SEQUENCE: 44

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 45
<211> LENGTH: 555
<212> TYPE: PRT
<213> ORGANISM: Artificial Sequence
<220> FEATURE:
<223> OTHER INFORMATION: RFP-RSV_18

<400> SEQUENCE: 45

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125
```

```
Ile Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
    210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Leu Phe Asp Ala Ser Ile Ser Gln Val Asn
                485                 490                 495
Glu Lys Ile Asn Gln Ser Leu Ala Trp Ile Arg Arg Ser Asp Glu Leu
            500                 505                 510
Leu His Asn Val Asn Thr Gly Lys Ser Thr Thr Asn Lys Leu Ser Gly
        515                 520                 525
Gly Tyr Ile Pro Glu Ala Pro Arg Asp Gly Gln Ala Tyr Val Arg Lys
    530                 535                 540
Asp Gly Glu Trp Val Leu Leu Ser Thr Phe Leu
```

545                 550              555

<210> SEQ ID NO 46
<211> LENGTH: 555
<212> TYPE: PRT
<213> ORGANISM: Artificial Sequence
<220> FEATURE:
<223> OTHER INFORMATION: RFP-RSV_19

<400> SEQUENCE: 46

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
```

-continued

```
            355                 360                 365
Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Trp Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu
545                 550                 555

<210> SEQ ID NO 47
<211> LENGTH: 555
<212> TYPE: PRT
<213> ORGANISM: Artificial Sequence
<220> FEATURE:
<223> OTHER INFORMATION: RFP-RSV_20

<400> SEQUENCE: 47

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
```

```
                165                 170                 175
Ala Val Val Ser Leu Ser Asn Gly Val Ser Val Gln Leu Ser Lys Val
                180                 185                 190

Leu Asp Leu Lys Asn Tyr Ile Asn Asn Gln Leu Leu Pro Ile Val Asn
                195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 48
<211> LENGTH: 555
<212> TYPE: PRT
<213> ORGANISM: Artificial Sequence
```

<220> FEATURE:
<223> OTHER INFORMATION: RFP-RSV_21

<400> SEQUENCE: 48

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400
```

```
Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu
545                 550                 555

<210> SEQ ID NO 49
<211> LENGTH: 725
<212> TYPE: PRT
<213> ORGANISM: Artificial Sequence
<220> FEATURE:
<223> OTHER INFORMATION: RFP-RSV_22

<400> SEQUENCE: 49

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205
```

```
Gln Gln Ser Cys Arg Ile Ser Asn Ile Glu Thr Val Ile Glu Phe Gln
    210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Lys Leu Ser Gly
        515                 520                 525
Gly Tyr Ile Pro Glu Ala Pro Arg Asp Gly Gln Ala Tyr Val Arg Lys
    530                 535                 540
Asp Gly Glu Trp Val Leu Leu Ser Thr Phe Leu Gly Gly Ser Thr
545                 550                 555                 560
Ser Asn Ile Lys Gly Leu Thr Gln Ala Ser Arg Asn Ala Asn Asp Gly
                565                 570                 575
Ile Ser Ile Ala Gln Thr Thr Glu Gly Ala Leu Asn Glu Ile Asn Asn
            580                 585                 590
Asn Leu Gln Arg Val Arg Glu Leu Ser Val Gln Ala Thr Asn Gly Thr
        595                 600                 605
Asn Ser Asp Ser Asp Leu Lys Ser Ile Gln Asp Glu Ile Gln Gln Arg
    610                 615                 620
```

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
            645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
            675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
            725

<210> SEQ ID NO 50
<211> LENGTH: 725
<212> TYPE: PRT
<213> ORGANISM: Artificial Sequence
<220> FEATURE:
<223> OTHER INFORMATION: RFP-RSV_23

<400> SEQUENCE: 50

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Ala Ala Gly Ala Ala Ala Gly Ala
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

```
Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
```

```
                        675                 680                 685
Leu Ala Ser Ile Asp Ser Ala Leu Ser Lys Val Asp Ala Val Arg Ser
        690                 695                 700
Ser Leu Gly Ala Ile Gln Asn Arg Phe Asp Ser Ala Ile Thr Asn Leu
705                 710                 715                 720
Gly Asn Thr Val Thr
                725

<210> SEQ ID NO 51
<211> LENGTH: 725
<212> TYPE: PRT
<213> ORGANISM: Artificial Sequence
<220> FEATURE:
<223> OTHER INFORMATION: RFP-RSV_24

<400> SEQUENCE: 51

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val

```
                305                 310                 315                 320
Leu Cys Thr Thr Asn Ile Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
                355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                    435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
                530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                    565                 570                 575

Ile Ser Ile Ala Gln Thr Thr Glu Gly Ala Leu Asn Glu Ile Asn Asn
                580                 585                 590

Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
            610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                    645                 650                 655

Asp Gly Glu Thr Ile Thr Ile Asp Leu Gln Lys Ile Asp Val Lys Ser
                660                 665                 670

Leu Gly Leu Asp Gly Phe Asn Val Asn Gly Gly Ser Thr Ala Asn Pro
            675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
                725
```

```
<210> SEQ ID NO 52
<211> LENGTH: 725
<212> TYPE: PRT
<213> ORGANISM: Artificial Sequence
<220> FEATURE:
<223> OTHER INFORMATION: RFP-RSV_25

<400> SEQUENCE: 52

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Asn Ser Gly Asn Ser Ser Gly Gly
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365
```

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
                515                 520                 525

Gly Tyr Ile Pro Glu Ala Pro Arg Asp Gly Gln Ala Tyr Val Arg Lys
                530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
                580                 585                 590

Asn Leu Gln Arg Val Arg Glu Leu Ser Val Gln Ala Thr Asn Gly Thr
                595                 600                 605

Asn Ser Asp Ser Asp Leu Lys Ser Ile Gln Asp Glu Ile Gln Gln Arg
                610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
                660                 665                 670

Leu Gly Leu Asp Gly Phe Asn Val Asn Gly Ser Thr Ala Asn Pro
                675                 680                 685

Leu Ala Ser Ile Asp Ser Ala Leu Ser Lys Val Asp Ala Val Arg Ser
                690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 53
<211> LENGTH: 725
<212> TYPE: PRT
<213> ORGANISM: Artificial Sequence
<220> FEATURE:
<223> OTHER INFORMATION: RFP-RSV_26

<400> SEQUENCE: 53

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Thr Leu Ser Lys Lys Arg Lys Arg
    130                 135                 140

Arg Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415
```

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
            530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
            565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
            610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
            645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
            675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
            725

<210> SEQ ID NO 54
<211> LENGTH: 725
<212> TYPE: PRT
<213> ORGANISM: Artificial Sequence
<220> FEATURE:
<223> OTHER INFORMATION: RFP-RSV_27

<400> SEQUENCE: 54

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
20 25 30

Tyr Gln Ser Thr Cys Ser Ala Val Ser Arg Gly Tyr Leu Ser Ala Leu
35 40 45

-continued

```
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
            115                 120                 125
Ile Ser Lys Lys Arg Lys Arg Arg Phe Leu Gly Trp Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
    195                 200                 205
Gln Gln Ser Cys Arg Ile Ser Asn Ile Glu Thr Val Ile Glu Phe Gln
210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
            245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
    275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
            355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Val Asn Lys Leu Glu Gly
    450                 455                 460
Lys Asn Leu Tyr Val Lys Gly Glu Pro Ile Ile Asn Tyr Tyr Asp Pro
```

```
                465                 470                 475                 480
Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Ser Thr Ala Asn Pro
        675                 680                 685

Leu Ala Ser Ile Asp Ser Ala Leu Ser Lys Val Asp Ala Val Arg Ser
                690                 695                 700

Ser Leu Gly Ala Ile Gln Asn Arg Phe Asp Ser Ala Ile Thr Asn Leu
705                 710                 715                 720

Gly Asn Thr Val Thr
            725

<210> SEQ ID NO 55
<211> LENGTH: 725
<212> TYPE: PRT
<213> ORGANISM: Artificial Sequence
<220> FEATURE:
<223> OTHER INFORMATION: RFP-RSV_28

<400> SEQUENCE: 55

Met Glu Leu Leu Ile His Arg Ser Ser Ala Ile Phe Leu Thr Leu Ala
1               5                   10                  15

Ile Asn Ala Ph

-continued

```
                100                 105                 110
Gln Tyr Met Asn Tyr Thr Ile Asn Thr Thr Lys Asn Leu Asn Val Ser
            115                 120                 125
Ile Ser Lys Lys Arg Lys Arg Arg Phe Leu Gly Phe Leu Leu Gly Val
        130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
            210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Lys Leu Ser Gly
        515                 520                 525
```

-continued

```
Gly Tyr Ile Pro Glu Ala Pro Arg Asp Gly Gln Ala Tyr Val Arg Lys
            530                 535                 540
Asp Gly Glu Trp Val Leu Leu Ser Thr Phe Leu Gly Gly Gly Ser Thr
545                 550                 555                 560
Ser Asn Ile Lys Gly Leu Thr Gln Ala Ser Arg Asn Ala Asn Asp Gly
                565                 570                 575
Ile Ser Ile Ala Gln Thr Thr Glu Gly Ala Leu Asn Glu Ile Asn Asn
            580                 585                 590
Asn Leu Gln Arg Val Arg Glu Leu Ser Val Gln Ala Thr Asn Gly Thr
            595                 600                 605
Asn Ser Asp Ser Asp Leu Lys Ser Ile Gln Asp Glu Ile Gln Gln Arg
610                 615                 620
Leu Glu Glu Ile Asp Arg Val Ser Asn Gln Thr Gln Phe Asn Gly Val
625                 630                 635                 640
Lys Val Leu Ser Gln Asp Asn Gln Met Lys Ile Gln Val Gly Ala Asn
                645                 650                 655
Asp Gly Glu Thr Ile Thr Ile Asp Leu Gln Lys Ile Asp Val Lys Ser
            660                 665                 670
Leu Gly Leu Asp Gly Phe Asn Val Asn Gly Gly Ser Thr Ala Asn Pro
            675                 680                 685
Leu Ala Ser Ile Asp Ser Ala Leu Ser Lys Val Asp Ala Val Arg Ser
690                 695                 700
Ser Leu Gly Ala Ile Gln Asn Arg Phe Asp Ser Ala Ile Thr Asn Leu
705                 710                 715                 720
Gly Asn Thr Val Thr
                725
```

<210> SEQ ID NO 56
<211> LENGTH: 725
<212> TYPE: PRT
<213> ORGANISM: Artificial Sequence
<220> FEATURE:
<223> OTHER INFORMATION: RFP-RSV_29

<400> SEQUENCE: 56

```
Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val Ser Arg Gly Tyr Leu Ser Ala Leu
            35                  40                  45
Arg Thr Gly Trp Tyr Thr Ser Val Ile Thr Ile Glu Leu Ser Asn Ile
50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
            115                 120                 125
Ile Ser Lys Lys Arg Lys Arg Arg Phe Leu Gly Phe Leu Leu Gly Val
130                 135                 140
Gly Ser Ala Ile Ala Ser Gly Ile Ala Val Ser Lys Val Leu His Leu
145                 150                 155                 160
```

```
Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
                195                 200                 205

Gln Gln Ser Cys Arg Ile Ser Asn Ile Glu Thr Val Ile Glu Phe Gln
                210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
                355                 360                 365

Thr Met Asn Ser Leu Thr Leu Pro Ser Glu Val Ser Leu Cys Asn Thr
                370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
                450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Ser Gly
                515                 520                 525

Gly Tyr Ile Pro Glu Ala Pro Arg Asp Gly Gln Ala Tyr Val Arg Lys
                530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575
```

-continued

```
Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
        610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
            645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
        690                 695                 700

Ser Leu Gly Ala Ile Gln Asn Arg Phe Asp Ser Ala Ile Thr Asn Leu
705                 710                 715                 720

Gly Asn Thr Val Thr
            725
```

<210> SEQ ID NO 57
<211> LENGTH: 725
<212> TYPE: PRT
<213> ORGANISM: Artificial Sequence
<220> FEATURE:
<223> OTHER INFORMATION: RFP-RSV_30

<400> SEQUENCE: 57

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Ala Asn Asn Arg Ala Arg Arg Glu Ala Pro
        100                 105                 110

Gln Tyr Met Asn Tyr Thr Ile Asn Thr Thr Lys Asn Leu Asn Val Ser
    115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Val Ser Leu Ser Asn Gly Val Ser Val Gln Thr Ser Lys Val
        180                 185                 190

Leu Asp Leu Lys Asn Tyr Ile Asn Asn Gln Leu Leu Pro Ile Val Asn
    195                 200                 205
```

-continued

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
610                 615                 620

Leu Glu Glu Ile Asp Arg Val Ser Asn Gln Thr Gln Phe Asn Gly Val

-continued

```
            625                 630                 635                 640
Lys Val Leu Ser Gln Asp Asn Gln Met Lys Ile Gln Val Gly Ala Asn
                    645                 650                 655

Asp Gly Glu Thr Ile Thr Ile Asp Leu Gln Lys Ile Asp Val Lys Ser
                660                 665                 670

Leu Gly Leu Asp Gly Phe Asn Val Asn Gly Gly Ser Thr Ala Asn Pro
                675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 58
<211> LENGTH: 725
<212> TYPE: PRT
<213> ORGANISM: Artificial Sequence
<220> FEATURE:
<223> OTHER INFORMATION: RFP-RSV_31

<400> SEQUENCE: 58

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
```

-continued

```
                260                 265                 270
Leu Met Ser Ser Asn Val Gln Ile Val Arg Gln Ser Tyr Ser Ile
            275                 280                 285
Met Ser Ile Ile Lys Glu Glu Val Leu Ala Tyr Val Gln Leu Pro
        290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Lys Leu Ser Gly
        515                 520                 525
Gly Tyr Ile Pro Glu Ala Pro Arg Asp Gly Gln Ala Tyr Val Arg Lys
    530                 535                 540
Asp Gly Glu Trp Val Leu Leu Ser Thr Phe Leu Gly Gly Gly Ser Thr
545                 550                 555                 560
Ser Asn Ile Lys Gly Leu Thr Gln Ala Ser Arg Asn Ala Asn Asp Gly
                565                 570                 575
Ile Ser Ile Ala Gln Thr Thr Glu Gly Ala Leu Asn Glu Ile Asn Asn
            580                 585                 590
Asn Leu Gln Arg Val Arg Glu Leu Ser Val Gln Ala Thr Asn Gly Thr
        595                 600                 605
Asn Ser Asp Ser Asp Leu Lys Ser Ile Gln Asp Glu Ile Gln Gln Arg
    610                 615                 620
Leu Glu Glu Ile Asp Arg Val Ser Asn Gln Thr Gln Phe Asn Gly Val
625                 630                 635                 640
Lys Val Leu Ser Gln Asp Asn Gln Met Lys Ile Gln Val Gly Ala Asn
                645                 650                 655
Asp Gly Glu Thr Ile Thr Ile Asp Leu Gln Lys Ile Asp Val Lys Ser
            660                 665                 670
Leu Gly Leu Asp Gly Phe Asn Val Asn Gly Gly Ser Thr Ala Asn Pro
        675                 680                 685
```

```
Leu Ala Ser Ile Asp Ser Ala Leu Ser Lys Val Asp Ala Val Arg Ser
        690                 695                 700
Ser Leu Gly Ala Ile Gln Asn Arg Phe Asp Ser Ala Ile Thr Asn Leu
705                 710                 715                 720
Gly Asn Thr Val Thr
                725

<210> SEQ ID NO 59
<211> LENGTH: 725
<212> TYPE: PRT
<213> ORGANISM: Artificial Sequence
<220> FEATURE:
<223> OTHER INFORMATION: RFP-RSV_32

<400> SEQUENCE: 59

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
                20                  25                  30
Tyr Gln Ser Thr Cys Ser Ala Val Ser Arg Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
        115                 120                 125
Ile Ser Lys Lys Arg Lys Arg Arg Phe Leu Gly Phe Leu Leu Gly Val
130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
```

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725
```

```
<210> SEQ ID NO 60
<211> LENGTH: 725
<212> TYPE: PRT
<213> ORGANISM: Artificial Sequence
<220> FEATURE:
<223> OTHER INFORMATION: RFP-RSV_33

<400> SEQUENCE: 60

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365
```

```
Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Ser Thr Ala Asn Pro
            675                 680                 685

Leu Ala Ser Ile Asp Ser Ala Leu Ser Lys Val Asp Ala Val Arg Ser
690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 61
<211> LENGTH: 725
<212> TYPE: PRT
<213> ORGANISM: Artificial Sequence
<220> FEATURE:
<223> OTHER INFORMATION: RFP-RSV_34

<400> SEQUENCE: 61
```

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Trp Leu Leu Gly Val
            130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
```

-continued

```
                420                 425                 430
Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 62
<211> LENGTH: 725
<212> TYPE: PRT
<213> ORGANISM: Artificial Sequence
<220> FEATURE:
<223> OTHER INFORMATION: RFP-RSV_35

<400> SEQUENCE: 62

Met Glu Leu Leu Ile His Arg Ser Ser Ala Ile Phe Leu Thr Leu Ala
1               5                   10                  15

Ile Asn Ala Phe Tyr Leu Thr Ser Ser Gln As

```
                50                  55                  60
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Trp Leu Leu Gly Val
        130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480
```

```
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 63
<211> LENGTH: 725
<212> TYPE: PRT
<213> ORGANISM: Artificial Sequence
<220> FEATURE:
<223> OTHER INFORMATION: RFP-RSV_36

<400> SEQUENCE: 63

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110
```

```
Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
            515                 520                 525
```

```
Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 64
<211> LENGTH: 725
<212> TYPE: PRT
<213> ORGANISM: Artificial Sequence
<220> FEATURE:
<223> OTHER INFORMATION: RFP-RSV_37

<400> SEQUENCE: 64

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Ph

```
Glu Gly Glu Val Asn Lys Ile Lys Asn Ala Leu Leu Ser Thr Asn Lys
              165                 170                 175

Ala Val Leu Ser Leu Ser Asn Gly Val Ser Val Leu Thr Ser Lys Val
          180                 185                 190

Leu Asp Leu Lys Asn Tyr Ile Asn Asn Gln Leu Leu Pro Ile Val Asn
              195                 200                 205

Gln Gln Ser Cys Arg Ile Ser Asn Ile Glu Thr Val Ile Glu Phe Gln
          210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
              245                 250                 255

Leu Leu Ser Leu Ile Asn Asp Met Pro Ile Thr Asn Asp Gln Lys Lys
          260                 265                 270

Leu Met Ser Ser Asn Val Gln Ile Val Arg Gln Gln Ser Tyr Ser Ile
          275                 280                 285

Met Ser Ile Ile Lys Glu Glu Val Leu Ala Tyr Val Val Gln Leu Pro
          290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
              325                 330                 335

Thr Asp Arg Gly Trp Tyr Cys Asp Asn Ala Gly Ser Val Ser Phe Phe
              340                 345                 350

Pro Gln Ala Asp Thr Cys Lys Val Gln Ser Asn Arg Val Phe Cys Asp
          355                 360                 365

Thr Met Asn Ser Leu Thr Leu Pro Ser Glu Val Ser Leu Cys Asn Thr
          370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
              405                 410                 415

Tyr Gly Lys Thr Lys Cys Thr Ala Ser Asn Lys Asn Arg Gly Ile Ile
              420                 425                 430

Lys Thr Phe Ser Asn Gly Cys Asp Tyr Val Ser Asn Lys Gly Val Asp
          435                 440                 445

Thr Val Ser Val Gly Asn Thr Leu Tyr Tyr Val Asn Lys Leu Glu Gly
          450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
              485                 490                 495

Glu Lys Ile Asn Gln Ser Leu Ala Phe Ile Arg Arg Ser Asp Glu Leu
              500                 505                 510

Leu His Asn Val Asn Thr Gly Lys Ser Thr Thr Asn Lys Leu Ser Gly
          515                 520                 525

Gly Tyr Ile Pro Glu Ala Pro Arg Asp Gly Gln Ala Tyr Val Arg Lys
          530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
              565                 570                 575

Ile Ser Ile Ala Gln Thr Thr Glu Gly Ala Leu Asn Glu Ile Asn Asn
```

580                 585                 590
Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
            645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
            675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
            725

<210> SEQ ID NO 65
<211> LENGTH: 725
<212> TYPE: PRT
<213> ORGANISM: Artificial Sequence
<220> FEATURE:
<223> OTHER INFORMATION: RFP-RSV_38

<400> SEQUENCE: 65

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln

```
            210                 215                 220
Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu Gly Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
                580                 585                 590

Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
        610                 615                 620

Leu Glu Glu Ile Asp Arg Val Ser Asn Gln Thr Gln Phe Asn Gly Val
625                 630                 635                 640
```

-continued

```
Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725
```

<210> SEQ ID NO 66
<211> LENGTH: 725
<212> TYPE: PRT
<213> ORGANISM: Artificial Sequence
<220> FEATURE:
<223> OTHER INFORMATION: RFP-RSV_39

<400> SEQUENCE: 66

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Ser Asn Val Gln Ile Val Arg Gln Ser Tyr Ser Ile
    275                 280                 285

Met Ser Ile Ile Lys Glu Glu Val Leu Ala Tyr Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                    485                 490                 495

Glu Lys Ile Asn Gln Ser Leu Ala Trp Ile Arg Arg Ser Asp Glu Leu
                500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
                580                 585                 590

Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                    645                 650                 655

Asp Gly Glu Thr Ile Thr Ile Asp Leu Gln Lys Ile Asp Val Lys Ser
                660                 665                 670

Leu Gly Leu Asp Gly Phe Asn Val Asn Gly Gly Ser Thr Ala Asn Pro
            675                 680                 685
```

```
Leu Ala Ser Ile Asp Ser Ala Leu Ser Lys Val Asp Ala Val Arg Ser
        690             695             700
Ser Leu Gly Ala Ile Gln Asn Arg Phe Asp Ser Ala Ile Thr Asn Leu
705             710             715             720
Gly Asn Thr Val Thr
            725

<210> SEQ ID NO 67
<211> LENGTH: 725
<212> TYPE: PRT
<213> ORGANISM: Artificial Sequence
<220> FEATURE:
<223> OTHER INFORMATION: RFP-RSV_40

<400> SEQUENCE: 67

Met Glu Leu Leu Ile His Arg Ser Ser Ala Ile Phe Leu Thr Leu Ala
1               5                   10                  15
Ile Asn Ala Phe Tyr Leu Thr Ser Ser Gln Asn Ile Thr Glu Glu Phe
            20                  25                  30
Tyr Gln Ser Thr Cys Ser Ala Val Ser Arg Gly Tyr Leu Ser Ala Leu
        35                  40                  45
Arg Thr Gly Trp Tyr Thr Ser Val Ile Thr Ile Glu Leu Ser Asn Ile
50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
        115                 120                 125
Ile Ser Lys Lys Arg Lys Arg Arg Phe Leu Gly Phe Leu Leu Gly Val
130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
```

-continued

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
    530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
    610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
    690                 695                 700

Ser Leu Gly Ala Ile Gln Asn Arg Phe Asp Ser Ala Ile Thr Asn Leu
705                 710                 715                 720

Gly Asn Thr Val Thr
                725
```

```
<210> SEQ ID NO 68
<211> LENGTH: 725
<212> TYPE: PRT
<213> ORGANISM: Artificial Sequence
<220> FEATURE:
<223> OTHER INFORMATION: RFP-RSV_41

<400> SEQUENCE: 68

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
```

```
                370                 375                 380
Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Ser Gly
        515                 520                 525

Gly Tyr Ile Pro Glu Ala Pro Arg Asp Gly Gln Ala Tyr Val Arg Lys
        530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
            565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
        595                 600                 605

Asn Ser Asp Ser Asp Leu Lys Ser Ile Gln Asp Glu Ile Gln Gln Arg
        610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Gly Ser Thr Ala Asn Pro
        675                 680                 685

Leu Ala Ser Ile Asp Ser Ala Leu Ser Lys Val Asp Ala Val Arg Ser
        690                 695                 700

Ser Leu Gly Ala Ile Gln Asn Arg Phe Asp Ser Ala Ile Thr Asn Leu
705                 710                 715                 720

Gly Asn Thr Val Thr
            725

<210> SEQ ID NO 69
<211> LENGTH: 725
<212> TYPE: PRT
<213> ORGANISM: Artificial Sequence
<220> FEATURE:
<223> OTHER INFORMATION: RFP-RSV_42

<400> SEQUENCE: 69

Met Glu Leu Leu Ile His Arg Ser Ser Ala Ile Phe Leu Thr Leu Ala
```

```
  1               5                   10                  15
Ile Asn Ala Phe Tyr Leu Thr Ser Ser Gln Asn Ile Thr Glu Glu Phe
                 20                  25                  30
Tyr Gln Ser Thr Cys Ser Ala Val Ser Arg Gly Tyr Leu Ser Ala Leu
                 35                  40                  45
Arg Thr Gly Trp Tyr Thr Ser Val Ile Thr Ile Glu Leu Ser Asn Ile
                 50                  55                  60
Lys Glu Thr Lys Cys Asn Gly Thr Asp Thr Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gln Asn Thr Pro Ala Ala Asn Asn Arg Ala Arg Arg Glu Ala Pro
                100                 105                 110
Gln Tyr Met Asn Tyr Thr Ile Asn Thr Thr Lys Asn Leu Asn Val Ser
                115                 120                 125
Ile Ser Lys Lys Arg Lys Arg Arg Phe Leu Gly Phe Leu Leu Gly Val
                130                 135                 140
Gly Ser Ala Ile Ala Ser Gly Ile Ala Val Ser Lys Val Leu His Leu
145                 150                 155                 160
Glu Gly Gln Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asn Asn Gln Leu Leu Pro Ile Val Asn
                195                 200                 205
Gln Gln Ser Cys Arg Ile Ser Asn Ile Glu Thr Val Ile Glu Phe Gln
                210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Ser Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
                290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
                355                 360                 365
Thr Met Asn Ser Leu Thr Leu Pro Ser Glu Val Ser Leu Cys Asn Thr
                370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
```

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Ser Gly
            515                 520                 525

Gly Tyr Ile Pro Glu Ala Pro Arg Asp Gly Gln Ala Tyr Val Arg Lys
            530                 535                 540

Asp Gly Glu Trp Val Leu Leu Ser Thr Phe Leu Gly Gly Ser Thr
545                 550                 555                 560

Ser Asn Ile Lys Gly Leu Thr Gln Ala Ser Arg Asn Ala Asn Asp Gly
                565                 570                 575

Ile Ser Ile Ala Gln Thr Thr Glu Gly Ala Leu Asn Glu Ile Asn Asn
            580                 585                 590

Asn Leu Gln Arg Val Arg Glu Leu Ser Val Gln Ala Thr Asn Gly Thr
            595                 600                 605

Asn Ser Asp Ser Asp Leu Lys Ser Ile Gln Asp Glu Ile Gln Gln Arg
            610                 615                 620

Leu Glu Glu Ile Asp Arg Val Ser Asn Gln Thr Gln Phe Asn Gly Val
625                 630                 635                 640

Lys Val Leu Ser Gln Asp Asn Gln Met Lys Ile Gln Val Gly Ala Asn
                645                 650                 655

Asp Gly Glu Thr Ile Thr Ile Asp Leu Gln Lys Ile Asp Val Lys Ser
            660                 665                 670

Leu Gly Leu Asp Gly Phe Asn Val Asn Gly Ser Thr Ala Asn Pro
            675                 680                 685

Leu Ala Ser Ile Asp Ser Ala Leu Ser Lys Val Asp Ala Val Arg Ser
            690                 695                 700

Ser Leu Gly Ala Ile Gln Asn Arg Phe Asp Ser Ala Ile Thr Asn Leu
705                 710                 715                 720

Gly Asn Thr Val Thr
                725

<210> SEQ ID NO 70
<211> LENGTH: 696
<212> TYPE: PRT
<213> ORGANISM: Artificial Sequence
<220> FEATURE:
<223> OTHER INFORMATION: RFP-RSV_43

<400> SEQUENCE: 70

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

-continued

```
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480
```

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 71
<211> LENGTH: 696
<212> TYPE: PRT
<213> ORGANISM: Artificial Sequence
<220> FEATURE:
<223> OTHER INFORMATION: RFP-RSV_44

<400> SEQUENCE: 71

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Ala Ala Gly Ala Ala Ala Gly Ala
    130                 135                 140

-continued

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn Lys Leu Gly Gly
    515                 520                 525

Gly Ser Thr Ser Asn Ile Lys Gly Leu Thr Gln Ala Ser Arg Asn Ala
530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr

```
                       565                 570                 575
Asn Gly Thr Asn Ser Asp Ser Asp Leu Lys Ser Ile Gln Asp Glu Ile
                   580                 585                 590

Gln Gln Arg Leu Glu Glu Ile Asp Arg Val Ser Asn Gln Thr Gln Phe
               595                 600                 605

Asn Gly Val Lys Val Leu Ser Gln Asp Asn Gln Met Lys Ile Gln Val
           610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                   645                 650                 655

Ala Asn Pro Leu Ala Ser Ile Asp Ser Ala Leu Ser Lys Val Asp Ala
               660                 665                 670

Val Arg Ser Ser Leu Gly Ala Ile Gln Asn Arg Phe Asp Ser Ala Ile
           675                 680                 685

Thr Asn Leu Gly Asn Thr Val Thr
           690                 695

<210> SEQ ID NO 72
<211> LENGTH: 696
<212> TYPE: PRT
<213> ORGANISM: Artificial Sequence
<220> FEATURE:
<223> OTHER INFORMATION: RFP-RSV_45

<400> SEQUENCE: 72

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
               20                  25                  30

Tyr Gln Ser Thr Cys Ser Ala Val Ser Arg Gly Tyr Leu Ser Ala Leu
           35                  40                  45

Arg Thr Gly Trp Tyr Thr Ser Val Ile Thr Ile Glu Leu Ser Asn Ile
       50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
               100                 105                 110

Gln Tyr Met Asn Tyr Thr Ile Asn Thr Thr Lys Asn Leu Asn Val Ser
           115                 120                 125

Ile Ser Lys Lys Arg Lys Arg Arg Gln Asn Gly Gln Asn Asn Gly Ser
       130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
               180                 185                 190

Leu Asp Leu Lys Asn Tyr Ile Asn Asn Gln Leu Leu Pro Ile Val Asn
           195                 200                 205

Gln Gln Ser Cys Arg Ile Ser Asn Ile Glu Thr Val Ile Glu Phe Gln
       210                 215                 220

Gln Lys Asn Ser Arg Leu Leu Glu Ile Thr Arg Glu Phe Ser Val Asn
```

```
            225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
                355                 360                 365

Thr Met Asn Ser Leu Thr Leu Pro Ser Glu Val Ser Leu Cys Asn Thr
                370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
                450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Lys Leu Gly Gly
                515                 520                 525

Gly Ser Thr Ser Asn Ile Lys Gly Leu Thr Gln Ala Ser Arg Asn Ala
                530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
                580                 585                 590

Gln Gln Arg Leu Glu Glu Ile Asp Arg Val Ser Asn Gln Thr Gln Phe
                595                 600                 605

Asn Gly Val Lys Val Leu Ser Gln Asp Asn Gln Met Lys Ile Gln Val
                610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655
```

```
Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
        690                 695

<210> SEQ ID NO 73
<211> LENGTH: 696
<212> TYPE: PRT
<213> ORGANISM: Artificial Sequence
<220> FEATURE:
<223> OTHER INFORMATION: RFP-RSV_46

<400> SEQUENCE: 73

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Asn Ser Gly Asn Ser Ser Gly Gly
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320
```

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 74
<211> LENGTH: 696
<212> TYPE: PRT
<213> ORGANISM: Artificial Sequence
<220> FEATURE:
```

<223> OTHER INFORMATION: RFP-RSV_47

<400> SEQUENCE: 74

Met Glu Leu Leu Ile His Arg Ser Ser Ala Ile Ph

-continued

```
Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695
```

<210> SEQ ID NO 75
<211> LENGTH: 696
<212> TYPE: PRT
<213> ORGANISM: Artificial Sequence
<220> FEATURE:
<223> OTHER INFORMATION: RFP-RSV_48

<400> SEQU

```
Lys Glu Thr Lys Cys Asn Gly Thr Asp Thr Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Trp Leu Leu Gly Val
            130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
```

```
                        485                 490                 495

Glu Lys Ile Asn Gln Ser Leu Ala Phe Ile Arg Arg Ser Asp Glu Leu
                    500                 505                 510

Leu His Asn Val Asn Thr Gly Lys Ser Thr Thr Asn Lys Leu Gly Gly
                515                 520                 525

Gly Ser Thr Ser Asn Ile Lys Gly Leu Thr Gln Ala Ser Arg Asn Ala
            530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
                580                 585                 590

Gln Gln Arg Leu Glu Glu Ile Asp Arg Val Ser Asn Gln Thr Gln Phe
                595                 600                 605

Asn Gly Val Lys Val Leu Ser Gln Asp Asn Gln Met Lys Ile Gln Val
                610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Ser Thr
                    645                 650                 655

Ala Asn Pro Leu Ala Ser Ile Asp Ser Ala Leu Ser Lys Val Asp Ala
                    660                 665                 670

Val Arg Ser Ser Leu Gly Ala Ile Gln Asn Arg Phe Asp Ser Ala Ile
                675                 680                 685

Thr Asn Leu Gly Asn Thr Val Thr
                690                 695

<210> SEQ ID NO 76
<211> LENGTH: 696
<212> TYPE: PRT
<213> ORGANISM: Artificial Sequence
<220> FEATURE:
<223> OTHER INFORMATION: RFP-RSV_49

<400> SEQUENCE: 76

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
```

```
            145                 150                 155                 160
Glu Gly Gln Val Asn Lys Ile Lys Asn Ala Leu Leu Ser Thr Asn Lys
                    165                 170                 175
Ala Val Val Ser Leu Ser Asn Gly Val Ser Val Leu Thr Ser Lys Val
                    180                 185                 190
Leu Asp Leu Lys Asn Tyr Ile Asn Asn Gln Leu Leu Pro Ile Val Asn
                    195                 200                 205
Gln Gln Ser Cys Arg Ile Ser Asn Ile Glu Thr Val Ile Glu Phe Gln
            210                 215                 220
Gln Lys Asn Ser Arg Leu Leu Glu Ile Thr Arg Glu Phe Ser Val Asn
225                 230                 235                 240
Ala Gly Val Thr Thr Pro Leu Ser Thr Tyr Met Leu Thr Asn Ser Glu
                    245                 250                 255
Leu Leu Ser Leu Ile Asn Asp Met Pro Ile Thr Asn Asp Gln Lys Lys
                    260                 265                 270
Leu Met Ser Ser Asn Val Gln Ile Val Arg Gln Gln Ser Tyr Ser Ile
                    275                 280                 285
Met Ser Ile Ile Lys Glu Glu Val Leu Ala Tyr Val Val Gln Leu Pro
            290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                    325                 330                 335
Thr Asp Arg Gly Trp Tyr Cys Asp Asn Ala Gly Ser Val Ser Phe Phe
                    340                 345                 350
Pro Gln Ala Asp Thr Cys Lys Val Gln Ser Asn Arg Val Phe Cys Asp
                    355                 360                 365
Thr Met Asn Ser Leu Thr Leu Pro Ser Glu Val Ser Leu Cys Asn Thr
            370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                    405                 410                 415
Tyr Gly Lys Thr Lys Cys Thr Ala Ser Asn Lys Asn Arg Gly Ile Ile
                    420                 425                 430
Lys Thr Phe Ser Asn Gly Cys Asp Tyr Val Ser Asn Lys Gly Val Asp
                    435                 440                 445
Thr Val Ser Val Gly Asn Thr Leu Tyr Tyr Val Asn Lys Leu Glu Gly
            450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                    485                 490                 495
Glu Lys Ile Asn Gln Ser Leu Ala Phe Ile Arg Arg Ser Asp Glu Leu
                    500                 505                 510
Leu His Asn Val Asn Thr Gly Lys Ser Thr Thr Asn Lys Leu Gly Gly
            515                 520                 525
Gly Ser Thr Ser Asn Ile Lys Gly Leu Thr Gln Ala Ser Arg Asn Ala
            530                 535                 540
Asn Asp Gly Ile Ser Ile Ala Gln Thr Thr Glu Gly Ala Leu Asn Glu
545                 550                 555                 560
Ile Asn Asn Asn Leu Gln Arg Val Arg Glu Leu Ser Val Gln Ala Thr
                    565                 570                 575
```

```
Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 77
<211> LENGTH: 696
<212> TYPE: PRT
<213> ORGANISM: Artificial Sequence
<220> FEATURE:
<223> OTHER INFORMATION: RFP-RSV_50

<400> SEQUENCE: 77

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240
```

-continued

```
Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655
```

```
Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
        690                 695

<210> SEQ ID NO 78
<211> LENGTH: 696
<212> TYPE: PRT
<213> ORGANISM: Artificial Sequence
<220> FEATURE:
<223> OTHER INFORMATION: RFP-RSV_51

<400> SEQUENCE: 78

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Arg Ala Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Gln Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320
```

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 79
<211> LENGTH: 696
<212> TYPE: PRT
<213> ORGANISM: Artificial Sequence
<220> FEATURE:
<223> OTHER INFORMATION: RFP-RSV_52
```

<400> SEQUENCE: 79

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys 405                 410                 415
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
            515                 520                 525

Gly Ser Thr Ser Asn Ile Lys Gly Leu Thr Gln Ala Ser Arg Asn Ala
            530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
            595                 600                 605

Asn Gly Val Lys Val Leu Ser Gln Asp Asn Gln Met Lys Ile Gln Val
            610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
            675                 680                 685

Thr Asn Leu Gly Asn Thr Val Thr
            690                 695

<210> SEQ ID NO 80
<211> LENGTH: 696
<212> TYPE: PRT
<213> ORGANISM: Artificial Sequence
<220> FEATURE:
<223> OTHER INFORMATION: RFP-RSV_53

<400> SEQUENCE: 80

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser

```
                65                  70                  75                  80
Gln Glu Leu Asp Lys Tyr Lys Asn Ala Val Thr Glu Leu Gln Leu Leu
                    85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
                115                 120                 125

Ile Ser Lys Lys Arg Lys Arg Arg Phe Leu Gly Phe Leu Leu Gly Val
            130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Gln Ser Tyr Ser Ile
            275                 280                 285

Met Ser Ile Ile Lys Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
                485                 490                 495
```

```
Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 81
<211> LENGTH: 696
<212> TYPE: PRT
<213> ORGANISM: Artificial Sequence
<220> FEATURE:
<223> OTHER INFORMATION: RFP-RSV_54

<400> SEQUENCE: 81

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160
```

```
Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Gly Gly
            515                 520                 525

Gly Ser Thr Ser Asn Ile Lys Gly Leu Thr Gln Ala Ser Arg Asn Ala
            530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
            565                 570                 575
```

```
Asn Gly Thr Asn Ser Asp Ser Asp Leu Lys Ser Ile Gln Asp Glu Ile
                580                 585                 590

Gln Gln Arg Leu Glu Glu Ile Asp Arg Val Ser Asn Gln Thr Gln Phe
            595                 600                 605

Asn Gly Val Lys Val Leu Ser Gln Asp Asn Gln Met Lys Ile Gln Val
        610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
            690                 695

<210> SEQ ID NO 82
<211> LENGTH: 696
<212> TYPE: PRT
<213> ORGANISM: Artificial Sequence
<220> FEATURE:
<223> OTHER INFORMATION: RFP-RSV_55

<400> SEQUENCE: 82

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240
```

```
Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
            275                 280                 285

Met Ser Ile Ile Lys Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
        530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
        610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
```

```
                660                 665                 670
Val Arg Ser Ser Leu Gly Ala Ile Gln Asn Arg Phe Asp Ser Ala Ile
            675                 680                 685

Thr Asn Leu Gly Asn Thr Val Thr
            690                 695

<210> SEQ ID NO 83
<211> LENGTH: 696
<212> TYPE: PRT
<213> ORGANISM: Artificial Sequence
<220> FEATURE:
<223> OTHER INFORMATION: RFP-RSV_56

<400> SEQUENCE: 83

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
```

```
                     325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
                355                 360                 365
Thr Met Asn Ser Leu Thr Leu Pro Ser Glu Val Ser Leu Cys Asn Thr
370                 375                 380
Asp Ile Phe Asn Ser Lys Tyr Asp Cys Lys Ile Met Thr Ser Lys Thr
385                 390                 395                 400
Asp Ile Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Leu Glu Gly
                450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
                500                 505                 510
Leu His Asn Val Asn Thr Gly Lys Ser Thr Thr Asn Lys Leu Gly Gly
                515                 520                 525
Gly Ser Thr Ser Asn Ile Lys Gly Leu Thr Gln Ala Ser Arg Asn Ala
                530                 535                 540
Asn Asp Gly Ile Ser Ile Ala Gln Thr Thr Glu Gly Ala Leu Asn Glu
545                 550                 555                 560
Ile Asn Asn Asn Leu Gln Arg Val Arg Glu Leu Ser Val Gln Ala Thr
                565                 570                 575
Asn Gly Thr Asn Ser Asp Ser Asp Leu Lys Ser Ile Gln Asp Glu Ile
                580                 585                 590
Gln Gln Arg Leu Glu Glu Ile Asp Arg Val Ser Asn Gln Thr Gln Phe
                595                 600                 605
Asn Gly Val Lys Val Leu Ser Gln Asp Asn Gln Met Lys Ile Gln Val
                610                 615                 620
Gly Ala Asn Asp Gly Glu Thr Ile Thr Ile Asp Leu Gln Lys Ile Asp
625                 630                 635                 640
Val Lys Ser Leu Gly Leu Asp Gly Phe Asn Val Asn Gly Gly Ser Thr
                645                 650                 655
Ala Asn Pro Leu Ala Ser Ile Asp Ser Ala Leu Ser Lys Val Asp Ala
                660                 665                 670
Val Arg Ser Ser Leu Gly Ala Ile Gln Asn Arg Phe Asp Ser Ala Ile
                675                 680                 685
Thr Asn Leu Gly Asn Thr Val Thr
690                 695
```

<210> SEQ ID NO 84
<211> LENGTH: 696
<212> TYPE: PRT
<213> ORGANISM: Artificial Sequence
<220> FEATURE:
<223> OTHER INFORMATION: RFP-RSV_57

```
<400> SEQUENCE: 84

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Lys Leu Gly Gly
            515                 520                 525

Gly Ser Thr Ser Asn Ile Lys Gly Leu Thr Gln Ala Ser Arg Asn Ala
            530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
            595                 600                 605

Asn Gly Val Lys Val Leu Ser Gln Asp Asn Gln Met Lys Ile Gln Val
            610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
            675                 680                 685

Thr Asn Leu Gly Asn Thr Val Thr
            690                 695

<210> SEQ ID NO 85
<211> LENGTH: 696
<212> TYPE: PRT
<213> ORGANISM: Artificial Sequence
<220> FEATURE:
<223> OTHER INFORMATION: RFP-RSV_58

<400> SEQUENCE: 85

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80
```

-continued

Gln Glu Leu Asp Lys Tyr Lys Asn Ala Val Thr Leu Gln Leu Leu
                    85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Leu Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Trp Asp Ala Ser Ile Ser Gln Val Asn
                485                 490                 495

```
Glu Lys Ile Asn Gln Ser Leu Ala Phe Ile Arg Arg Ser Asp Glu Leu
            500                 505                 510

Leu His Asn Val Asn Thr Gly Lys Ser Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
            595                 600                 605

Asn Gly Val Lys Val Leu Ser Gln Asp Asn Gln Met Lys Ile Gln Val
        610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
            675                 680                 685

Thr Asn Leu Gly Asn Thr Val Thr
            690                 695

<210> SEQ ID NO 86
<211> LENGTH: 696
<212> TYPE: PRT
<213> ORGANISM: Artificial Sequence
<220> FEATURE:
<223> OTHER INFORMATION: RFP-RSV_59

<400> SEQUENCE: 86

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Trp Leu Leu Gly Val
    130                 135                 140

Gly Ser Ala Ile Ala Ser Gly Ile Ala Val Ser Lys Val Leu His Leu
145                 150                 155                 160
```

-continued

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Asp Thr Cys Lys Val Gln Ser Asn Arg Val Phe Cys Asp
    355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Trp Ile Arg Arg Ser Asp Glu Leu
        500                 505                 510

Leu His Asn Val Asn Thr Gly Lys Ser Thr Thr Asn Lys Leu Gly Gly
    515                 520                 525

Gly Ser Thr Ser Asn Ile Lys Gly Leu Thr Gln Ala Ser Arg Asn Ala
530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
            565                 570                 575

Asn Gly Thr Asn Ser Asp Ser Asp Leu Lys Ser Ile Gln Asp Glu Ile

```
                580             585             590
Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
        610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
        690                 695

<210> SEQ ID NO 87
<211> LENGTH: 696
<212> TYPE: PRT
<213> ORGANISM: Artificial Sequence
<220> FEATURE:
<223> OTHER INFORMATION: RFP-RSV_60

<400

```
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
            290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
            355                 360                 365
Thr Met Asn Ser Leu Thr Leu Pro Ser Glu Val Ser Leu Cys Asn Thr
            370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Leu Glu Gly
            450                 455                 460
Lys Asn Leu Tyr Val Lys Gly Glu Pro Ile Ile Asn Tyr Tyr Asp Pro
465                 470                 475                 480
Leu Val Phe Pro Ser Asp Leu Phe Asp Ala Ser Ile Ser Gln Val Asn
            485                 490                 495
Glu Lys Ile Asn Gln Ser Leu Ala Trp Ile Arg Arg Ser Asp Glu Leu
            500                 505                 510
Leu His Asn Val Asn Thr Gly Lys Ser Thr Thr Asn Lys Leu Gly Gly
            515                 520                 525
Gly Ser Thr Ser Asn Ile Lys Gly Leu Thr Gln Ala Ser Arg Asn Ala
            530                 535                 540
Asn Asp Gly Ile Ser Ile Ala Gln Thr Thr Glu Gly Ala Leu Asn Glu
545                 550                 555                 560
Ile Asn Asn Asn Leu Gln Arg Val Arg Glu Leu Ser Val Gln Ala Thr
            565                 570                 575
Asn Gly Thr Asn Ser Asp Ser Asp Leu Lys Ser Ile Gln Asp Glu Ile
            580                 585                 590
Gln Gln Arg Leu Glu Glu Ile Asp Arg Val Ser Asn Gln Thr Gln Phe
            595                 600                 605
Asn Gly Val Lys Val Leu Ser Gln Asp Asn Gln Met Lys Ile Gln Val
            610                 615                 620
Gly Ala Asn Asp Gly Glu Thr Ile Thr Ile Asp Leu Gln Lys Ile Asp
625                 630                 635                 640
Val Lys Ser Leu Gly Leu Asp Gly Phe Asn Val Asn Gly Gly Ser Thr
            645                 650                 655
Ala Asn Pro Leu Ala Ser Ile Asp Ser Ala Leu Ser Lys Val Asp Ala
            660                 665                 670
```

Val Arg Ser Ser Leu Gly Ala Ile Gln Asn Arg Phe Asp Ser Ala Ile
    675                 680                 685

Thr Asn Leu Gly Asn Thr Val Thr
    690                 695

<210> SEQ ID NO 88
<211> LENGTH: 696
<212> TYPE: PRT
<213> ORGANISM: Artificial Sequence
<220> FEATURE:
<223> OTHER INFORMATION: RFP-RSV_61

<400> SEQUENCE: 88

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

-continued

```
Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Gly Gly
            515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
            595                 600                 605

Asn Gly Val Lys Val Leu Ser Gln Asp Asn Gln Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
            675                 680                 685

Thr Asn Leu Gly Asn Thr Val Thr
    690                 695
```

<210> SEQ ID NO 89
<211> LENGTH: 696
<212> TYPE: PRT
<213> ORGANISM: Artificial Sequence
<220> FEATURE:
<223> OTHER INFORMATION: RFP-RSV_62

<400> SEQUENCE: 89

```
Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65              70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
                100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Gln Leu Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Trp Ile Arg Arg Ser Asp Glu Leu
            500                 505                 510

Leu His Asn Val Asn Thr Gly Lys Ser Thr Thr Asn Lys Leu Gly Gly
        515                 520                 525

Gly Ser Thr Ser Asn Ile Lys Gly Leu Thr Gln Ala Ser Arg Asn Ala
    530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Met Lys Ile Gln Val
    610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
    690                 695

<210> SEQ ID NO 90
<211> LENGTH: 696
<212> TYPE: PRT
<213> ORGANISM: Artificial Sequence
<220> FEATURE:
<223> OTHER INFORMATION: RFP-RSV_63

<400> SEQUENCE: 90

Met Glu Leu Leu Ile His Arg Ser Ser Ala Ile Phe Leu Thr Leu Ala
1               5                   10                  15

Ile Asn Ala Phe Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80
```

```
Gln Glu Leu Asp Lys Tyr Lys Asn Ala Val Thr Glu Leu Gln Leu Leu
             85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Gln Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Leu Phe Asp Ala Ser Ile Ser Gln Val Asn
            485                 490                 495

Glu Lys Ile Asn Gln Ser Leu Ala Phe Ile Arg Arg Ser Asp Glu Leu
```

```
                500             505             510
Leu His Asn Val Asn Thr Gly Lys Ser Thr Thr Asn Lys Leu Gly Gly
            515                 520                 525

Gly Ser Thr Ser Asn Ile Lys Gly Leu Thr Gln Ala Ser Arg Asn Ala
        530                 535                 540

Asn Asp Gly Ile Ser Ile Ala Gln Thr Thr Glu Gly Ala Leu Asn Glu
545                 550                 555                 560

Ile Asn Asn Asn Leu Gln Arg Val Arg Glu Leu Ser Val Gln Ala Thr
                565                 570                 575

Asn Gly Thr Asn Ser Asp Ser Asp Leu Lys Ser Ile Gln Asp Glu Ile
            580                 585                 590

Gln Gln Arg Leu Glu Glu Ile Asp Arg Val Ser Asn Gln Thr Gln Phe
        595                 600                 605

Asn Gly Val Lys Val Leu Ser Gln Asp Asn Gln Met Lys Ile Gln Val
        610                 615                 620

Gly Ala Asn Asp Gly Glu Thr Ile Thr Ile Asp Leu Gln Lys Ile Asp
625                 630                 635                 640

Val Lys Ser Leu Gly Leu Asp Gly Phe Asn Val Asn Gly Gly Ser Thr
                645                 650                 655

Ala Asn Pro Leu Ala Ser Ile Asp Ser Ala Leu Ser Lys Val Asp Ala
            660                 665                 670

Val Arg Ser Ser Leu Gly Ala Ile Gln Asn Arg Phe Asp Ser Ala Ile
        675                 680                 685

Thr Asn Leu Gly Asn Thr Val Thr
        690                 695

<210> SEQ ID NO 91
<211> LENGTH: 1668
<212> TYPE: DNA
<213> ORGANISM: Artificial Sequence
<220> FEATURE:
<223> OTHER INFORMATION: RFP-RSV_4_NT

<400> SEQUENCE: 91
atggagctcc tgatccaccg ttcctccgct atcttcctga ccctggctat caacgctttt    60
tacctgacca gctcccagaa catcactgag gagttttacc agtccacctg ctccgccgtg   120
tcccgtggtt acctctccgc tctgcgcacc ggttggtata cctccgtgat tactattgag   180
ctgagcaata tcaaagaaac caaatgcaat ggcaccgaca ccaaagtgaa actgattaag   240
caagagctcg acaagtataa gaatgctgtc accgaactgc agctgctcat gcaaaacact   300
cctgctgcta caaccgtgc ccgtcgtgag ctccccagt acatgaacta caccatcaac    360
accaccaaga acctgaatgt gtccatctcc aagaagcgca acgtcgtaa ctcgggtaac    420 tcgtccggtg gaggctccgc catcgcttct ggtatcgctg tctccaaggt gctgcacctg   480
gaaggtgagg tgaacaagat caaaaacgct ctgctgtcca ccaacaaggc tgtcgtgtcc   540
ctgtccaatg gcgtgtctgt cctcacctct aaagtgctgg acctgaagaa ctatattaac   600
aaccagctgc tccccatcgt gaatcagcag tcctgccgta tttccaacat cgaaaccgtc   660
attgaattcc agcagaagaa ctcccgtctg ctcgagatca cccgcgaatt ctccgtgaac   720
gctggtgtga ccactcctct gtctacctac atgctgacca actccgagct gctgtccctc   780
atcaatgata tgcccattac caacgaccag aaaaaactga tgtcctccaa tgtccagatc   840
gtgcgtcagc agtcctactc catcatgtcc attatcaagg aggaggtcct ggcttatgtg   900
gtgcagctgc ccatctatgg tgtgattgat acccctgct ggaaactgca cacttcccct   960
```

```
ctgtgcacca ccaacatcaa ggaaggctcc aatatctgtc tgactcgtac cgaccgtggt   1020
tggtactgtg acaatgccgg ttccgtctcc ttctttcccc aggctgacac ctgcaaagtg   1080
cagtccaacc gtgtgttctg tgacaccatg aactccctca ctctgccctc cgaagtgtcc   1140
ctgtgcaaca ccgacatttt caattccaag tatgactgca agatcatgac ctctaaaacc   1200
gacatctcct cctccgtgat tacctccctg ggcgctattg tgtcctgcta tggtaaaact   1260
aagtgcaccg cctccaacaa aaatcgtggt atcattaaga ccttttccaa tggttgtgat   1320
tacgtgtcca caaaggtgt cgataccgtc tccgtgggta acactctcta ctatgtgaac   1380
aagctggagg gcaagaacct ctacgtgaaa ggtgaaccta tcattaacta ctatgacccc   1440
ctggtgtttc cctctgatga gtttgacgct tccatttccc aagtgaatga gaaaatcaat   1500
caaagcctgg ctttcattcg tcgttccgat gaactgctcc ataacgtgaa tactggtaaa   1560
tccaccacca acaagctttc cggaggttac atccccgagg ctccccgtga cggtcaggct   1620
tacgtgcgta aggacggtga gtgggtgctg ctgtccacct tcctgtaa                1668

<210> SEQ ID NO 92
<211> LENGTH: 2091
<212> TYPE: DNA
<213> ORGANISM: Artificial Sequence
<220> FEATURE:
<223> OTHER INFORMATION: RFP-RSV_46_NT

<400> SEQUENCE: 92
atggagctcc tgatccaccg ttcctccgct atcttcctga ccctggctat caacgctttt   60
tacctgacca gctcccagaa catcactgag gagttttacc agtccacctg ctccgccgtg   120
tcccgtggtt acctctccgc tctgcgcacc ggttggtata cctccgtgat tactattgag   180
ctgagcaata tcaaagaaac caaatgcaat ggcaccgaca ccaaagtgaa actgattaag   240
caagagctcg acaagtataa gaatgctgtc accgaactgc agctgctcat gcaaaacact   300
cctgctgcta acaaccgtgc ccgtcgtgag gctccccagt acatgaacta caccatcaac   360
accaccaaga acctgaatgt gtccatctcc aagaagcgca aacgtcgtaa ctcgggtaac   420
tcgtccggtg gaggctccgc catcgcttct ggtatcgctg tctccaaggt gctgcacctg   480
gaaggtgagg tgaacaagat caaaaacgct ctgctgtcca ccaacaaggc tgtcgtgtcc   540
ctgtccaatg gcgtgtctgt cctcacctct aaagtgctgg acctgaagaa ctatattaac   600
aaccagctgc tccccatcgt gaatcagcag tcctgccgta tttccaacat cgaaaccgtc   660
attgaattcc agcagaagaa ctcccgtctg ctcgagatca cccgcgaatt ctccgtgaac   720
gctggtgtga ccactcctct gtctacctac atgctgacca actccgagct gctgtccctc   780
atcaatgata tgcccattac caacgaccag aaaaaactga tgtcctccaa tgtccagatc   840
gtgcgtcagc agtcctactc catcatgtcc attatcaagg aggaggtcct ggcttatgtg   900
gtgcagctgc ccatctatgg tgtgattgat acccctgct ggaaactgca cacttcccct   960
ctgtgcacca ccaacatcaa ggaaggctcc aatatctgtc tgactcgtac cgaccgtggt   1020
tggtactgtg acaatgccgg ttccgtctcc ttctttcccc aggctgacac ctgcaaagtg   1080
cagtccaacc gtgtgttctg tgacaccatg aactccctca ctctgccctc cgaagtgtcc   1140
ctgtgcaaca ccgacatttt caattccaag tatgactgca agatcatgac ctctaaaacc   1200
gacatctcct cctccgtgat tacctccctg ggcgctattg tgtcctgcta tggtaaaact   1260
aagtgcaccg cctccaacaa aaatcgtggt atcattaaga ccttttccaa tggttgtgat   1320
```

| | |
|---|---:|
| tacgtgtcca acaaaggtgt cgataccgtc tccgtgggta acactctcta ctatgtgaac | 1380 |
| aagctggagg gcaagaacct ctacgtgaaa ggtgaaccta tcattaacta ctatgacccc | 1440 |
| ctggtgtttc cctctgatga gtttgacgct tccatttccc aagtgaatga gaaaatcaat | 1500 |
| caaagcctgg ctttcattcg tcgttccgat gaactgctcc ataacgtgaa tactggtaaa | 1560 |
| tccaccacca acaagcttgg tggtggttcc acctccaaca tcaagggtct gacccaggct | 1620 |
| tcccgtaacg ctaacgacgg tatctccatc gctcagacca ccgagggtgc tctgaacgag | 1680 |
| atcaacaaca acctgcagcg tgtgcgtgag ctgtccgtgc aggctaccaa cggtaccaac | 1740 |
| tccgactccg acctgaagtc catccaggac gagatccagc agcgtctgga ggagatcgac | 1800 |
| cgtgtgtcca accagaccca gttcaacggt gtgaaggtgc tgtcccagga caaccagatg | 1860 |
| aagatccagg tgggtgctaa cgacggtgag accatcacca tcgacctgca gaagatcgac | 1920 |
| gtgaagtccc tgggtctgga cggtttcaac gtgaacggtg gttccaccgc taacccctg | 1980 |
| gcttccatcg actccgctct gtccaaggtg gacgctgtgc gttcctccct gggtgctatc | 2040 |
| cagaaccgtt tcgactccgc tatcaccaac ctgggtaaca ccgtgaccta a | 2091 |

<210> SEQ ID NO 93
<211> LENGTH: 2178
<212> TYPE: DNA
<213> ORGANISM: Artificial Sequence
<220> FEATURE:
<223> OTHER INFORMATION: RFP-RSV_25_NT

<400> SEQUENCE: 93

| | |
|---|---:|
| atggagctcc tgatccaccg ttcctccgct atcttcctga ccctggctat caacgctttt | 60 |
| tacctgacca gctcccagaa catcactgag gagttttacc agtccacctg ctccgccgtg | 120 |
| tcccgtggtt acctctccgc tctgcgcacc ggttggtata cctccgtgat tactattgag | 180 |
| ctgagcaata tcaaagaaac caaatgcaat ggcaccgaca ccaaagtgaa actgattaag | 240 |
| caagagctcg acaagtataa gaatgctgtc accgaactgc agctgctcat gcaaaacact | 300 |
| cctgctgcta caaccgtgc ccgtcgtgag ctccccagt acatgaacta caccatcaac | 360 |
| accaccaaga acctgaatgt gtccatctcc aagaagcgca acgtcgtaa ctcgggtaac | 420 |
| tcgtccggtg gaggctccgc catcgcttct ggtatcgctg tctccaaggt gctgcacctg | 480 |
| gaaggtgagt gaacaagat caaaaacgct ctgctgtcca ccaacaaggc tgtcgtgtcc | 540 |
| ctgtccaatg gcgtgtctgt cctcacctct aaagtgctgg acctgaagaa ctatattaac | 600 |
| aaccagctgc tccccatcgt gaatcagcag tcctgccgta tttccaacat cgaaaccgtc | 660 |
| attgaattcc agcagaagaa ctcccgtctg ctcgagatca cccgcgaatt ctccgtgaac | 720 |
| gctggtgtga ccactcctct gtctacctac atgctgacca actccgagct gctgtccctc | 780 |
| atcaatgata tgcccattac caacgaccag aaaaaactga tgtcctccaa tgtccagatc | 840 |
| gtgcgtcagc agtcctactc catcatgtcc attatcaagg aggaggtcct ggcttatgtg | 900 |
| gtgcagctgc ccatctatgg tgtgattgat accccctgct ggaaactgca cacttcccct | 960 |
| ctgtgcacca ccaacatcaa ggaaggctcc aatatctgtc tgactcgtac cgaccgtggt | 1020 |
| tggtactgtg acaatgccgg ttccgtctcc ttctttcccc aggctgacac ctgcaaagtg | 1080 |
| cagtccaacc gtgtgttctg tgacaccatg aactccctca ctctgccctc cgaagtgtcc | 1140 |
| ctgtgcaaca ccgacatttt caattccaag tatgactgca agatcatgac ctctaaaacc | 1200 |
| gacatctcct cctccgtgat tacctccctg ggcgctattg tgtcctgcta tggtaaaact | 1260 |
| aagtgcaccg cctccaacaa aaatcgtggt atcattaaga ccttttccaa tggttgtgat | 1320 |

```
tacgtgtcca acaaaggtgt cgataccgtc tccgtgggta acactctcta ctatgtgaac    1380
aagctggagg gcaagaacct ctacgtgaaa ggtgaaccta tcattaacta ctatgacccc    1440
ctggtgtttc cctctgatga gtttgacgct tccatttccc aagtgaatga gaaaatcaat    1500
caaagcctgg ctttcattcg tcgttccgat gaactgctcc ataacgtgaa tactggtaaa    1560
tccaccacca acaagctttc cggaggttac atccccgagg ctccccgtga cggtcaggct    1620
tacgtgcgta aggacggtga gtgggtgctg ctgtccacct tcctgggtgg tggttccacc    1680
tccaacatca agggtctgac ccaggcttcc cgtaacgcta acgacggtat ctccatcgct    1740
cagaccaccg agggtgctct gaacgagatc aacaacaacc tgcagcgtgt gcgtgagctg    1800
tccgtgcagg ctaccaacgg taccaactcc gactccgacc tgaagtccat ccaggacgag    1860
atccagcagc gtctggagga gatcgaccgt gtgtccaacc agacccagtt caacggtgtg    1920
aaggtgctgt cccaggacaa ccagatgaag atccaggtgg gtgctaacga cggtgagacc    1980
atcaccatcg acctgcagaa gatcgacgtg aagtccctgg gtctggacgg tttcaacgtg    2040
aacggtggtt ccaccgctaa ccccctggct tccatcgact ccgctctgtc caaggtggac    2100
gctgtgcgtt cctccctggg tgctatccag aaccgtttcg actccgctat caccaacctg    2160
ggtaacaccg tgacctaa                                                  2178

<210> SEQ ID NO 94
<211> LENGTH: 501
<212> TYPE: DNA
<213> ORGANISM: Artificial Sequence
<220> FEATURE:
<223> OTHER INFORMATION: Codon Optimized SK_fla

<400> SEQUENCE: 94
acctccaaca tcaagggtct gacccaggct tcccgtaacg ctaacgacgg tatctccatc     60
gctcagacca ccgagggtgc tctgaacgag atcaacaaca acctgcagcg tgtgcgtgag    120
ctgtccgtgc aggctaccaa cggtaccaac tccgactccg acctgaagtc catccaggac    180
gagatccagc agcgtctgga ggagatcgac cgtgtgtcca accagaccca gttcaacggt    240
gtgaaggtgc tgtcccagga caaccagatg aagatccagg tgggtgctaa cgacggtgag    300
accatcacca tcgacctgca gaagatcgac gtgaagtccc tgggtctgga cggtttcaac    360
gtgaacggtg gttccaccgc taaccccctg gcttccatcg actccgctct gtccaaggtg    420
gacgctgtgc gttcctccct gggtgctatc cagaaccgtt tcgactccgc tatcaccaac    480
ctgggtaaca ccgtgaccta a                                              501

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Ala Ala Gly Ala Ala Ala Gly Ala Gly
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 96

Gln Asn Gly Gln Asn Asn Gly Ser Gly
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

Asn Ser Gly Asn Ser Ser Gly Gly Gly
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Thr Leu Ser Lys Lys Arg Lys Arg Arg
1               5

<210> SEQ ID NO 99
<211> LENGTH: 4
<212> TYPE: PRT
<213> ORGANISM: Artificial Sequence
<220> FEATURE:
<223> OTHER INFORMATION: Synthetic peptide

<400> SEQUENCE: 99

Lys Leu Ser Gly
1

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Gly Gly Gly Ser
1

<210> SEQ ID NO 101
<211> LENGTH: 6
<212> TYPE: PRT
<213> ORGANISM: Artificial Sequence
<220> FEATURE:
<223> OTHER INFORMATION: Synthetic peptide

<400> SEQUENCE: 101

Lys Leu Gly Gly Gly Ser
1               5

<210> SEQ ID NO 102
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 102

Arg Ala Arg Arg
1

<210> SEQ ID NO 103
<211> LENGTH: 6
<212> TYPE: PRT
<213> ORGANISM: Artificial Sequence
<220> FEATURE:
<223> OTHER INFORMATION: Synthetic peptide

<400> SEQUENCE: 103

Lys Lys Arg Lys Arg Arg
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic peptide

<400> SEQUENCE: 104

Phe Leu Gly Phe Leu Leu Gly Val Gly
1               5
```